United States Patent
Aoki et al.

(10) Patent No.: US 9,232,884 B2
(45) Date of Patent: Jan. 12, 2016

(54) CAPSULE MEDICAL APPARATUS AND MEDICAL SYSTEM

(75) Inventors: Isao Aoki, Hachioji (JP); Miho Katayama, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 1439 days.

(21) Appl. No.: 12/418,780

(22) Filed: Apr. 6, 2009

(65) Prior Publication Data

US 2009/0253999 A1    Oct. 8, 2009

(30) Foreign Application Priority Data

Apr. 7, 2008 (JP) .................................. 2008-099481

(51) Int. Cl.

| A61B 1/04 | (2006.01) |
|---|---|
| A61B 1/00 | (2006.01) |
| A61B 10/02 | (2006.01) |
| A61B 5/07 | (2006.01) |
| A61B 10/06 | (2006.01) |
| A61B 19/00 | (2006.01) |

(52) U.S. Cl.
CPC ............... *A61B 1/041* (2013.01); *A61B 1/0005* (2013.01); *A61B 1/00016* (2013.01); *A61B 1/00158* (2013.01); *A61B 5/073* (2013.01); *A61B 10/02* (2013.01); *A61B 10/06* (2013.01); *A61B 2019/2265* (2013.01); *A61B 2562/0238* (2013.01); *A61B 2562/162* (2013.01)

(58) Field of Classification Search
CPC ........ A61B 1/041; A61B 10/02; A61B 10/06; A61B 2562/0238; A61B 2562/162
USPC ......... 600/562–571, 101, 103, 104, 109, 114, 600/117, 118, 153, 156, 160, 587
See application file for complete search history.

(56) References Cited

U.S. PATENT DOCUMENTS

| 2001/0051766 A1 | 12/2001 | Gazdzinski |
|---|---|---|
| 2003/0167000 A1* | 9/2003 | Mullick et al. ................. 600/424 |
| 2004/0176664 A1 | 9/2004 | Iddan |
| 2005/0154277 A1 | 7/2005 | Tang et al. |
| 2005/0272972 A1* | 12/2005 | Iddan ............................ 600/102 |

FOREIGN PATENT DOCUMENTS

| JP | 2000-116657 | 4/2000 |
|---|---|---|
| JP | 2003-111763 | 4/2003 |
| JP | 2003-325438 | 11/2003 |
| JP | 2005-040204 | 2/2005 |
| JP | 2006-512130 A | 4/2006 |
| JP | 2007-303915 A | 11/2007 |
| JP | 2007-537817 A | 12/2007 |
| JP | 2008-501466 A | 1/2008 |
| WO | WO 2004/058041 A2 | 7/2004 |
| WO | WO 2005/112460 A2 | 11/2005 |
| WO | WO 2005/120325 A2 | 12/2005 |

OTHER PUBLICATIONS

Notice of Rejection dated Dec. 18, 2012 from corresponding Japanese Patent Application No. 2008-099481 together with an English language translation.

* cited by examiner

*Primary Examiner* — Devin Henson
(74) *Attorney, Agent, or Firm* — Scully, Scott, Murphy & Presser, P.C.

(57) ABSTRACT

A capsule medical apparatus includes a tissue obtaining unit that obtains a tissue from a body site of a subject; a detecting unit that detects a state of the tissue obtaining unit that varies depending on whether the tissue obtaining unit succeeds in obtaining a tissue; an output unit that outputs information representing whether the tissue obtaining unit succeeds in obtaining a tissue; and a control unit that determines whether the tissue obtaining unit succeeds in obtaining a tissue based on the state of the tissue obtaining unit, which is detected by the detecting unit, and causes the output unit to output the information representing whether the tissue obtaining unit succeeds in obtaining a tissue.

2 Claims, 21 Drawing Sheets

(PHASE A1)

(PHASE A2)

(PHASE A3)

(PHASE A4)

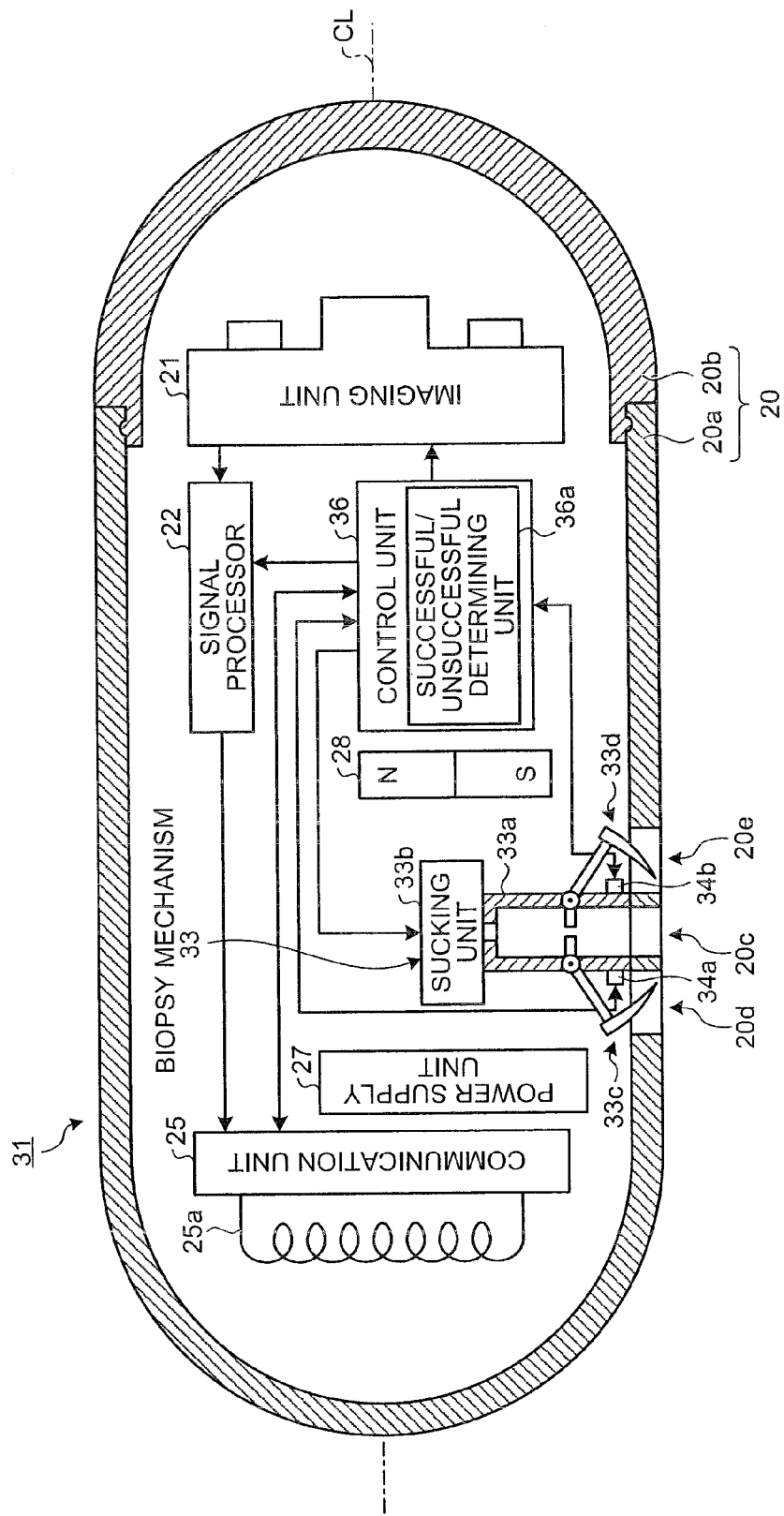

(PHASE B1)

(PHASE B2)

(PHASE B3)

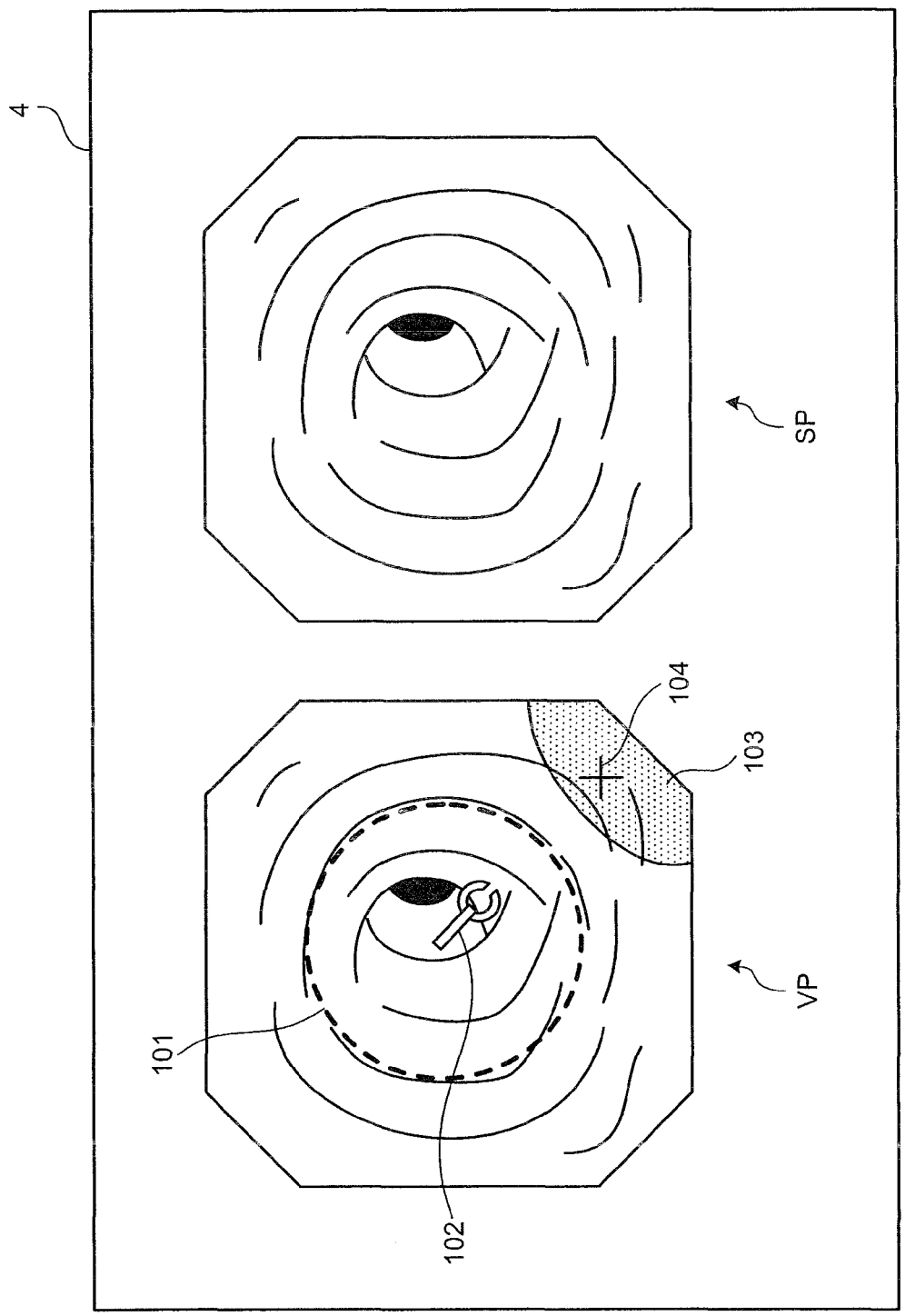

(PHASE C1)

(PHASE C2)

(PHASE C3)

(PHASE C4)

(PHASE C5)

(PHASE C6)

(PHASE C7)

(PHASE C8)

CAPSULE MEDICAL APPARATUS AND MEDICAL SYSTEM

CROSS-REFERENCE TO RELATED APPLICATIONS

This application is based upon and claims the benefit of priority from Japanese Patent Application No. 2008-099481, filed Apr. 7, 2008, the entire contents of which are incorporated herein by reference.

BACKGROUND OF THE INVENTION

1. Field of the Invention

The present invention relates to a capsule medical apparatus and a medical system and, more particularly, to a capsule medical apparatus that is introduced into a subject to obtain a tissue from a body site (site to be examined) in order to perform a biopsy, such as a pathological diagnosis.

2. Description of the Related Art

Capsule endoscopes are available in the field of capsule endoscopy that are introduced into the organs of a subject and images (hereinafter, "in-vivo images") of the inside of internal organs. These capsule endoscopes have image capturing and wireless communication functions. A subject, such as a patient, swallows a capsule endoscope, which then moves through the alimentary canal due to peristalsis. As the capsule endoscope moves, it captures in-vivo images of the subject. Each time the capsule endoscope captures in-vivo images, it wirelessly transmits the in-vivo images sequentially to a receiving device outside the subject. The capsule endoscope is eventually discharged to the outside with excrement.

An example of the kind of capsule endoscope described above includes a capsule medical apparatus that includes a tool, such as a forceps-shaped cup or a brush, for obtaining a tissue at the site to be examined (target site) in the subject (see Japanese Patent Application Laid-open No. 2003-325438). When the conventional capsule medical apparatus disclosed in Japanese Patent Application Laid open No. 2003-325438 is introduced into a subject and has reached a target site, the tissue-sampling tool takes a tissue. The tissue-sampling tool is operated by a rotating magnetic field, which is applied from outside the subject.

Various types of medical systems for performing medical procedures, such as obtaining or excising tissue from a body site of a subject, have been developed in the field of capsule endoscopy. For example, a medical system is known in which ultrasound cross-sectional images that represent a puncture needle inserted into a target site in a subject are displayed so that the user can confirm that the puncture needle is actually inserted into the target site (see Japanese Patent Application Laid-open No. 2005-40204). A capsule endoscope is also known in which an observing unit is provided to a suturing member that sutures a tissue, for example, a wound in the large intestine from which a lesion has been excised, so that the user can observe the suture (see Japanese Patent Application Laid-open No. 2003-111763). A capsule endoscope is also known in which an image converter, such as an ultrasonic sensor, is arranged on a tube that is inserted into the tissue of a subject (see Japanese Patent Application Laid-open No. 2000-116657). Using the technology disclosed in Japanese Patent Application Laid-open No. 2000-116657, information from an image converter is displayed on a display device, which allows the user to confirm whether an affected area is excised appropriately.

SUMMARY OF THE INVENTION

A capsule medical apparatus according to one aspect of the present invention includes a tissue obtaining unit that obtains a tissue from a body site of a subject; a detecting unit that detects a state of the tissue obtaining unit that varies depending on whether the tissue obtaining unit succeeds in obtaining a tissue; an output unit that outputs information representing whether the tissue obtaining unit succeeds in obtaining a tissue to outside of the subject; and a control unit that determines whether the tissue obtaining unit succeeds in obtaining a tissue based on the state of the tissue obtaining unit, which is detected by the detecting unit, and causes the output unit to output the information representing whether the tissue obtaining unit succeeds in obtaining a tissue.

A medical system according to another aspect of the present invention includes a capsule medical apparatus that is introduced into a subject, performs a series of obtaining operations for obtaining a tissue from a body site of the subject, and transmits successful/unsuccessful information that represents whether a tissue is successfully obtained to outside the subject; a receiving unit that receives the successful/unsuccessful information transmitted from the capsule medical apparatus; a display unit that displays the successful/unsuccessful information; and a first control unit that controls the series of obtaining operations, receives the successful/unsuccessful information via the receiving unit, and causes the display unit to display the successful/unsuccessful information.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 6 is a schematic diagram of a configuration example of a capsule medical apparatus according to a second embodiment of the present invention;

FIG. 16 is a schematic diagram of a specific example of a virtual image displayed by an external display unit;

DETAILED DESCRIPTION OF THE PREFERRED EMBODIMENTS

Exemplary embodiments of the present invention are explained in detail below with reference to the accompanying drawings.

Figure 1:
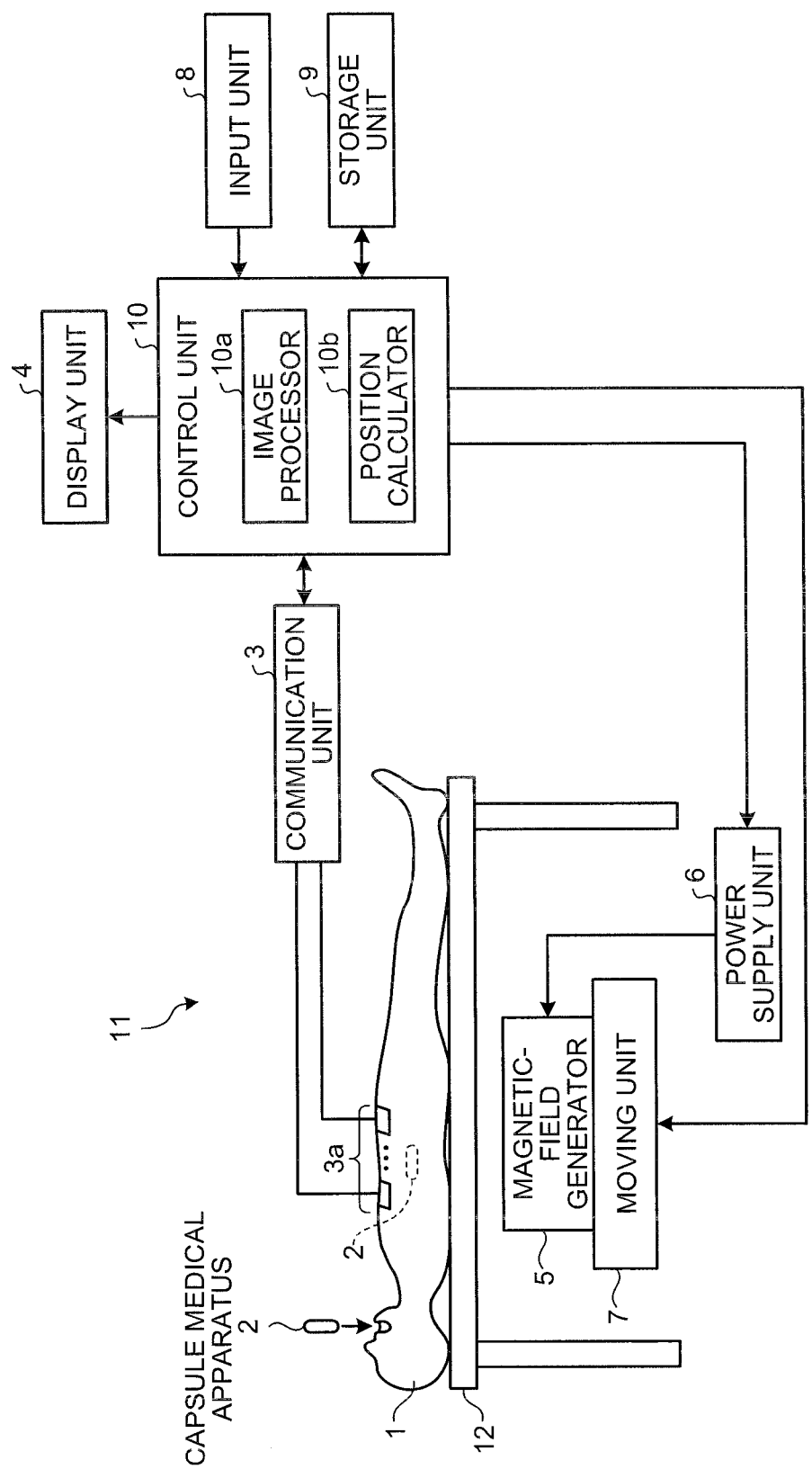
FIG. 1 is a block diagram that schematically represents a configuration example of a medical system according to a first embodiment of the present invention.

FIG. 1 is a block diagram that schematically shows a configuration example of a medical system according to a first embodiment of the present invention. A medical system 11 according to the first embodiment is a system in which a capsule medical apparatus is introduced into a subject and the capsule medical apparatus obtains a tissue from a desired body site in the subject. Specifically, as shown in FIG. 1, the medical system 11 includes a capsule medical apparatus 2, a communication unit 3, and a display unit 4. The capsule medical apparatus 2 is introduced into a subject 1 such as a patient and then obtains a tissue in the subject 1. The communication unit 3 wirelessly communicates with the capsule medical apparatus 2 in the subject 1 via a plurality of antennas 3a arranged on the body surface of the subject 1. The display unit 4 displays various types of information including in-vivo images of the subject 1 captured by the capsule medical apparatus 2. The medical system 11 further includes a magnetic-field generator 5 that generates a magnetic field for guiding the capsule medical apparatus 2 in the subject 1; a power supply unit 6 that supplies power to the magnetic-field generator 5; and a moving unit 7 that moves the magnetic-field generator 5. The medical system 11 further includes an input unit 8 that inputs various types of information; a storage unit 9 that stores therein various types of information including in-vivo images of the subject 1; and a control unit 10 that controls each unit of the medical system 11.

The capsule medical apparatus 2 is formed in a capsule-like shape and in a size such that it can be introduced into the subject 1. The capsule medical apparatus 2 has a tissue obtaining function for obtaining a tissue from a body site in the subject 1, and a wireless communication function for wirelessly communicating with external devices. Specifically, the capsule medical apparatus 2 is introduced into the subject 1 from the mouth of the subject 1, and it moves through the alimentary canal of the subject 1 due to peristalsis or an external magnetic field. When the capsule medical apparatus 2 reaches a desired body site (a body site to be examined by performing a biopsy such as a pathological diagnosis) in the subject 1, the capsule medical apparatus 2 then performs a series of obtaining operations for obtaining a tissue from the body site based on instructions issued from an external unit (specifically, a control signal from the control unit 10) and wirelessly transmits successful/unsuccessful information representing whether a tissue is successfully obtained each time the series of obtaining operations is performed. When the capsule medical apparatus 2 succeeds in obtaining a tissue from the body site, it completes the series of obtaining operations and stores the obtained tissue in a capsule casing. Thereafter, the capsule medical apparatus 2 moves through the alimentary canal of the subject 1 due to peristalsis or an external magnetic field, and discharged to outside the subject 1 eventually. The tissue obtained by the capsule medical apparatus 2 is then taken out of the capsule casing in order to perform a biopsy such as a pathological diagnosis.

The capsule medical apparatus 2 has an image capturing function for capturing in-vivo images of the subject 1. The capsule medical apparatus 2 sequentially captures in-vivo images of the subject 1 while moving through the alimentary canal of the subject 1 due to peristalsis or an external magnetic field. Each time the capsule medical apparatus 2 captures an in-vivo image, it wirelessly transmits image signals containing the in-vivo images sequentially to outside the subject 1.

The communication unit 3 is connected to the antennas 3a arranged on the body surface of the subject 1, and it wirelessly communicates with the capsule medical apparatus 2 in the subject 1 via any one of the antennas 3a. The communication unit 3 receives wireless signals from the capsule medical apparatus 2 via the antennas 3a, and performs a demodulating process on the received wireless signals to extract the image signal or the successful/unsuccessful information. The communication unit 3 transmits various types of information including the extracted image signal and the successful/unsuccessful information to the control unit 10. The communication unit 3 also receives a control signal for controlling the capsule medical apparatus 2 from the control unit 10, and performs a predetermined modulating process on the received control signal to generate a wireless signal containing the control signal. The communication unit 3 transmits the generated wireless signal to the capsule medical apparatus 2 in the subject 1 via the antenna 3a.

The image signal extracted (demodulated) by the communication unit 3 contains the in-vivo image captured by the capsule medical apparatus 2 in the subject 1. The successful/unsuccessful information extracted by the communication unit 3 represents whether the capsule medical apparatus 2 in the subject 1 succeeds in obtaining a tissue.

The antennas 3a are receiving/transmitting antennas used for wireless communications between the capsule medical apparatus 2 introduced into the subject 1 and the communication unit 3 outside the subject 1. The antennas 3a are arranged separately on the body surface of the subject 1 into which the capsule medical apparatus 2 is introduced. At least one of the antennas 3a captures a wireless signal from the capsule medical apparatus 2 positioned in the subject 1 (for example, in the alimentary canal such as the esophagus, the stomach, the small intestine, or the large intestine) and transmits the wireless signal to the communication unit 3. In addition, at least one of the antennas 3a transmits a wireless signal from the communication unit 3 to the capsule medical apparatus 2 in the subject 1.

Various types of displays including a CRT display or a liquid crystal display can be used for the display unit 4. The display unit 4 displays various types of information that the control unit 10 instructs the display unit 4 to display. Specifically, the display unit 4 displays a group of in-vivo images of the subject 1 captured by the capsule medical apparatus 2. The display unit 4 also displays patient information and examination information about the subject 1 that are input by the input unit 8. The display unit 4 also displays positional information about the capsule medical apparatus 2 in the subject 1 and the successful/unsuccessful information representing whether the capsule medical apparatus 2 succeeds in obtaining a tissue.

The magnetic-field generator 5 includes a plurality of magnets. The magnetic-field generator 5 generates a three-dimensional external magnetic field such as a rotating magnetic field or a gradient magnetic field due to a power supplied to the magnetic-field generator 5 from the power supply unit 6. The magnetic-field generator 5 applies the external magnetic field to the capsule medical apparatus 2 in the subject 1 that is laid on a bed 12. The magnetic-field generator 5 guides the capsule medical apparatus 2 to a desired body site in the subject 1 or causes the capsule medical apparatus 2 to be pressed against the body site by the magnetic field.

The power supply unit 6 supplies, to the magnetic-field generator 5, a power for forming an external magnetic field to be applied to the capsule medical apparatus 2 in the subject 1. Specifically, the power supply unit 6 supplies an electric current to the magnetic-field generator 5 under the control by the control unit 10, which causes the magnetic-field generator 5 to form a three-dimensional magnetic field such as a rotating magnetic field or a gradient magnetic field. In other words, the external magnetic field generated by the magnetic-field generator 5 is controlled by the electric current supplied from the power supply unit 6 (the amount of power received from the power supply unit 6). To generate a rotating magnetic field, it suffices that alternating currents with different phases be supplied to the magnets of the magnetic-field generator 5, respectively.

The moving unit 7 moves the magnetic-field generator 5 relatively to the subject 1 such that the external magnetic field generated by the magnetic-field generator 5 is applied to the capsule medical apparatus 2 in the subject 1. Specifically, an X-Y plane approximately parallel to the surface of the bed 12 on which the subject 1 is laid is set, and the moving unit 7 moves the magnetic-field generator 5 to a coordinate position in the X-Y plane under the control by the control unit 10. The moving unit 7 moves the magnetic-field generator 5 such that the capsule medical apparatus 2 in the subject 1 is positioned in the three-dimensional space in which the external magnetic field is formed by the magnetic-field generator 5. In the first embodiment, the moving unit 7 moves the magnetic-field generator 5. Alternatively, a moving unit may be provided to the bed 12. In this case, by moving the bed 12, the magnetic-field generator 5 and the subject 1 are moved relatively to each other.

The input unit 8 is, for example, an input device such as a keyboard, a mouse, or a joy stick. The input unit 8 inputs various types of information corresponding to input operations by a user such as a doctor or a nurse to the control unit 10. The input unit 8 also functions as an operating unit that performs an operation for controlling the control unit 10 based on the information displayed on the display unit 4 (the in-vivo images or the successful/unsuccessful information). The various types of information input by the input unit 8 to the control unit 10 includes instruction information about instructions to the control unit 10, patient information about the subject, and examination information about the subject. The patient information about the subject identifies the subject, and it includes the patient name of the subject, patient ID, date of birth, sex, and age. The examination information about the patient identifies biological examination carried out using a tissue that is obtained from a body part by the capsule medical apparatus 2 introduced into the subject, and it includes the examination ID and examination date.

Various types of storage media such as a RAM, an EEPROM, a flash memory, and a hard disk, each of which stores therein rewritable information, can be used for the storage unit 9. The storage unit 9 stores therein various types of information that the control unit 10 instructs the storage unit 9 to store, and sends information that the control unit 10 instructs the storage unit to read to the control unit 10. The storage unit 9 stores therein a group of in-vivo images of the subject 1, patient information and examination information about the subject 1, and current position information about the capsule medical apparatus 2 in the subject 1 under the control by the control unit 10.

The control unit 10 controls the units (the capsule medical apparatus 2, the communication unit 3, the display unit 4, the magnetic-field generator 5, the power supply unit 6, the moving unit 7, the input unit 8, and the storage unit 9) of the medical system 11, and controls input and output of signals between the above units of the medical system 11. Specifically, the control unit 10 controls operations of each of the communication unit 3, the display unit 4, the moving unit 7, and the storage unit 9 based on the instruction information input by the input unit 8. The control unit 10 controls the amount of power to be received by the magnetic-field generator 5 from the power supply unit 6 to control the direction and strength of the magnetic field generated by the magnetic-field generator 5. The control unit 10 controls the magnetic-field generator 5 to control magnetic induction of the capsule medical apparatus 2 in the subject 1. The control unit 10 generates a control signal for instructing the capsule medical apparatus 2 to perform the series of obtaining operations for obtaining a tissue from the body site, based on the instruction information input by the input unit 8. The instruction information is for instructing the capsule medical apparatus 2 in the subject 1 to perform the series of obtaining operations. The control unit 10 controls the communication unit 3 to transmit the control signal to the capsule medical apparatus 2 in the subject 1, and controls the capsule medical apparatus 2 in the subject 1 using the control signal.

The control unit 10 includes an image processor 10a that generates an in-vivo image of the subject 1, and a position calculator 10b that calculates a position of the capsule medical apparatus 2 in the subject 1. The image processor 10a receives, from the communication unit 3, the image signal obtained by demodulating the wireless signal from the capsule medical apparatus 2. The image processor 10a performs predetermined image processing on the received image signal to generate (reconstitutes) the image information corresponding to the image signal, i.e., the in-vivo image of the subject 1. The group of in-vivo images generated by the image processor 10a are displayed on the display unit 4 and stored in the storage unit 9 as described above.

The position calculator 10b receives, from the communication unit 3, a received field strength of each of the antennas 3a via which the communication unit 3 sequentially receives the wireless signals from the capsule medical apparatus 2. For example, the position calculator 10b receives the top three received field strengths of antennas out of the antennas 3a. The position calculator 10b calculates the current position of the capsule medical apparatus 2 in the subject 1 based on the received field strengths and the position information about the antennas 3a, using, for example, trigonometry. The control unit 10 associates the current position information about the current information, which is calculated by the position calculator 10b, with the in-vivo images of the subject 1 captured by the capsule medical apparatus 2 existing in the current position. The in-vivo images of the subject 1 and the current position information of the capsule medical apparatus 2, which are associated with each other by the control unit 10, are displayed on the display unit 4 and stored in the storage unit 9.

Figure 2:
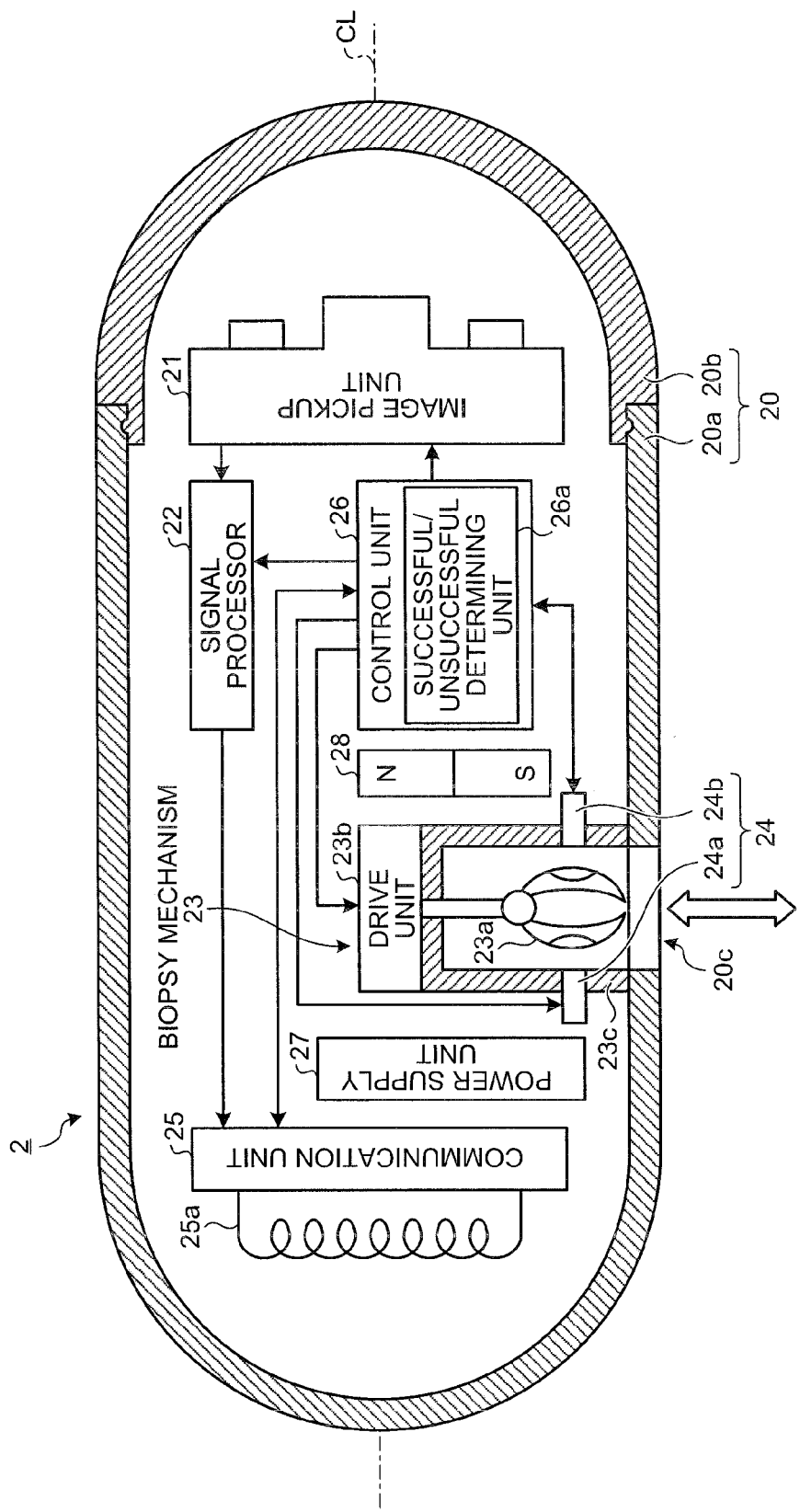
FIG. 2 is a schematic diagram of a configuration example of a capsule medical apparatus according to the first embodiment.
Figure 3:
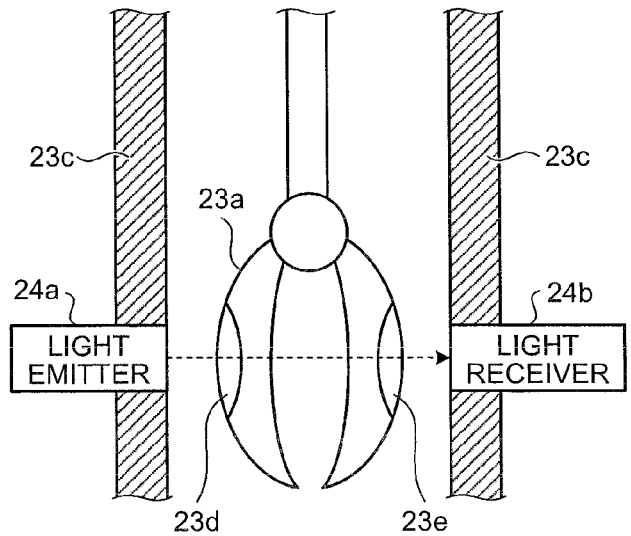
FIG. 3 is a schematic diagram of an enlarged view of an obtaining unit of a tissue obtaining unit that is incorporated in the capsule medical apparatus.

A configuration of the capsule medical apparatus 2 according to the first embodiment of the present invention is explained in detail below. FIG. 2 is a schematic diagram of a configuration example of the capsule medical apparatus according to the first embodiment of the present invention. FIG. 3 is a schematic diagram of an enlarged view of an obtaining unit of a tissue obtaining unit that is incorporated in the capsule medical apparatus. As shown in FIGS. 2 and 3, the capsule medical apparatus 2 according to the first embodiment includes a capsule casing 20, an imaging unit 21, a signal processor 22, a biopsy mechanism 23, and a photosensor 24. The capsule casing 20 includes a cylindrical casing 20a and a dome-shaped casing 20b. The imaging unit 21 captures in-vivo images of the subject 1. The signal processor 22 generates an image signal containing the in-vivo image captured by the imaging unit 21. The biopsy mechanism 23 obtains a tissue from a body site. The photosensor 24 detects whether there is a tissue obtained by the biopsy mechanism 23. The capsule medical apparatus 2 further includes a communication unit 25, a control unit 26, a power unit 27, and a magnet 28. The communication unit 25 wirelessly communicates with the communication unit 3 (see FIG. 1) outside the subject 1. The control unit 26 controls each unit of the capsule medical apparatus 2. The power unit 27 is, for example, a battery. The magnet 28 moves in accordance with the external magnetic field generated by the magnetic-field generator 5.

The capsule casing 20 is a casing that is formed in a capsule-like shape and in a size such that it can be introduced into the subject 1. The capsule casing 20 is formed in a way that one (open end) of the ends of the cylindrical casing 20a whose other end has a dome-like shape is closed with the dome-shaped casing 20b. The dome-shaped casing 20b is an optical dome that has transparency to light in a predetermined wavelength band (for example, visible light). In contrast, the cylindrical casing 20a is opaque, and an opening 20c for obtaining a tissue from the body site is formed in a part of the cylindrical casing 20a. The imaging unit 21, the signal processor 22, the biopsy mechanism 23, the photosensor 24, the communication unit 25, the control unit 26, the power unit 27, and the magnet 28 are housed in the capsule casing 20 including the cylindrical casing 20a and the dome-shaped casing 20b. The biopsy mechanism 23 is arranged near the opening 20c of the capsule casing 20.

The imaging unit 21 captures in-vivo images of the subject 1, and it includes an illuminating unit such as an LED, an optical system such as a collective lens, and an imaging device such as a fixed image-pickup device. The imaging unit 21 applies light to a subject (specifically, the inside of an internal organ of the subject 1) via the dome-shaped casing 20b, and collects the light reflected from the subject to form an optical image of the subject on a receiving surface of the imaging device. The imaging unit 21 obtains the formed optical image of the subject, i.e., captures an in-vivo image of the subject 1. The signal processor 22 receives a signal that is obtained by converting the light by the imaging unit 21, and performs predetermined signal processing on the received signal to generate an image signal containing the in-vivo image of the subject 1.

The biopsy mechanism 23 functions as a tissue obtaining unit that obtains a tissue from the body site of the subject 1. The biopsy mechanism 23 obtains a tissue by performing the series of obtaining operations under the control by the control unit 26. The biopsy mechanism 23 includes a forceps-shaped obtaining unit 23a that obtains a tissue by excising it from the body site of the subject 1; a drive unit 23b that causes the obtaining unit 23a to operate; and a housing unit 23c that houses therein the obtaining unit 23a.

The obtaining unit 23a is forceps-shaped as shown in FIG. 2, and it performs the series of obtaining operations for obtaining a tissue from a body site due to the action of the drive unit 23b. Specifically, the obtaining unit 23a is housed in the housing unit 23c in the capsule casing 20, and it protrudes to outside the capsule casing 20 from the opening 20c due to the action of the drive unit 23b. After the obtaining unit 23a protrudes a predetermined distance (for example, a sufficient distance with which the obtaining unit 23a contacts with the body site of the subject 1), it opens or closes its forceps-shaped tips due to the action of the drive unit 23b to excise a tissue from the body site of the subject 1, thereby obtaining the excised tissue. Thereafter, while holding the tissue, the obtaining unit 23a moves into the capsule casing 20 due to the action of the drive unit 23b and is housed in the housing unit 23c eventually. In this manner, the obtaining unit 23a completes one cycle of the series of obtaining operations. The tissue obtained by the obtaining unit 23a and held in the forceps-shaped tips of the obtaining unit 23a is stored in the capsule casing 20.

As shown in FIGS. 2 and 3, a pair of openings 23d and 23e that allows light to be communicated between a light emitter 24a and a light receiver 24b of the photosensor 24 is formed in the forceps-shaped tips of the obtaining unit 23a. The openings 23d and 23e are formed to be linearly opposed to each other. If no tissue is held (obtained) in the forceps-shaped tips of the obtaining unit 23a when the obtaining unit 23a is housed in the housing unit 23c, light can be emitted from the light emitter 24a and received by the light receiver 24b via the forceps-shaped tips of the obtaining unit 23a.

The drive unit 23b is, for example, an actuator, and it causes the obtaining unit 23a to perform the series of obtaining operations under the control by the control unit 26. Each time the drive unit 23b receives a control signal from the control unit 26, i.e., for each time of the control by the control unit 26, the drive unit 23b causes the obtaining unit 23a to perform one cycle of the series of obtaining operations.

The housing unit 23c is a cylindrical member that houses therein the obtaining unit 23a, and it is arranged near the opening 20c of the capsule casing 20. The housing unit 23c communicates with outside the capsule casing 20 via the opening 20c, and it partitions a space into an internal area of the capsule casing 20 in which electric devices including the control unit 26 and the power unit 27 are housed, and an area in which the obtaining unit 23a is housed. The light emitter 24a and the light receiver 24b of the photosensor 24 are arranged on the wall of the housing unit 23c.

The photosensor 24 functions as a detecting unit that detects the state of the biopsy mechanism 23 that varies depending on whether the biopsy mechanism 23 succeeds in obtaining a tissue. Specifically, the photosensor 24 includes the light emitter 24a and the light receiver 24b. The photosensor 24 optically detects the state of the biopsy mechanism 23, for example, whether there is a tissue obtained by the obtaining unit 23a of the biopsy mechanism 23, based on a light communicated between the light emitter 24a and the light receiver 24b.

The light emitter 24a and the light receiver 24b are arranged on the wall of the housing unit 23c such that the light emitter 24a and the light receiver 24b are linearly opposed to each other. As shown in FIGS. 2 and 3, the light emitter 24a and the light receiver 24b are opposed to the openings 23d and 23e of the obtaining unit 23a, respectively, when the obtaining unit 23a is housed in the housing unit 23c. The light emitter 24a emits predetermined light toward the light receiver 24b under the control by the control unit 26. When no tissue is held by the forceps-shaped tips of the obtaining unit 23a, the light emitted by the light emitter 24a passes through the openings 23d and 23e of the obtaining unit 23a sequentially and then received by the light receiver 24b (see the dotted line shown in FIG. 3). In contrast, when a tissue is held by the forceps-shaped tips of the obtaining unit 23a, the light passes through the opening 23d of the obtaining unit 23a and is then blocked by the tissue in the obtaining unit 23a. The light receiver 24b enters a phase where it can receive a light from the light emitter 24a at light-emitting timing of the light emitter 24a under the control by the control unit 26. The light receiver 24b receives the light from the light emitter 24a when no tissue is held in the forceps-shaped tips of the obtaining unit 23a. In contrast, the light receiver 24b does not receive the light from the light emitter 24a when a tissue is held in the forceps-shaped tips of the obtaining unit 23a. Upon receiving light from the light emitter 24a, the light receiver 24b transmits, to the control unit 26, an electric signal (hereinafter, "detection signal") corresponding to the received light as a result of detecting whether there is a tissue obtained by the obtaining unit 23a of the biopsy mechanism 23.

The communication unit 25 includes a coil-shaped antenna 25a, and it communicates with the communication unit 3 (see FIG. 1) outside the subject 1 with the antenna 25a. Specifically, the communication unit 25 wirelessly transmits the in-vivo images of the subject 1 to the outside under the control by the control unit 26. More specifically, the communication unit 25 receives the image signal generated by the signal processor 22, performs a predetermined modulating process on the image signal to generate a wireless signal including the image signal, and transmits the generated wireless signal to the outside. The communication unit 25 also wirelessly transmits the successful/unsuccessful information, which represents whether the biopsy mechanism 23 succeeds in obtaining a tissue, under the control by the control unit 26. Specifically, the communication unit 25 receives the successful/unsuccessful information from the control unit 26, performs the predetermined modulating process on the successful/unsuccessful information to generate a wireless signal containing the successful/unsuccessful information, and transmits the wireless signal to the outside. The wireless signal containing the image signal or the successful/unsuccessful information is received by the communication unit 3 via the antennas 3a.

The communication unit 25 receives the wireless signal from the communication unit 3 via the antenna 25a under the control by the control unit 26, performs the predetermined demodulating process on the wireless signal to extract the control signal contained in the wireless signal. As described above, the control signal obtained by demodulation by the communication unit 25 is a control signal generated by the control unit 10 outside the subject 1 and a control signal for instructing the capsule medical apparatus to perform the series of obtaining operations for obtaining a tissue from the body site. The communication unit 25 transmits the control signal from the control unit 10 outside the subject 1 to the control unit 26.

The control unit 26 controls the units (the imaging unit 21, the signal processor 22, the biopsy mechanism 23, the photosensor 24, and the communication unit 25) of the capsule medical apparatus 2, and controls input and output of signals communicated between the above units. Specifically, the control unit 26 controls the imaging unit 21 to captures images (i.e., in-vivo images) of a subject illuminated with light. The control unit 26 controls the signal processor 22 and the communication unit 25 to wirelessly transmit the image signal containing the in-vivo image of the subject 1 captured by the imaging unit 21 to the outside. The control unit 26 receives the control signal from the control unit 10 outside the subject 1 via the communication unit 25, and controls the series of obtaining operations of the biopsy mechanism 23 based on the received control signal. The control unit 26 controls the drive unit 23b of the biopsy mechanism 23 based on the control signal, and controls the operations of the obtaining unit 23a, i.e., the series of obtaining operations through the control on the drive unit 23b.

The control unit 26 includes a successful/unsuccessful determining unit 26a that determines whether the obtaining unit 23a of the biopsy mechanism 23 succeeds in obtaining a tissue. The successful/unsuccessful determining unit 26a determines whether the obtaining unit 23a succeeds in obtaining a tissue, based on the state of the biopsy mechanism 23 detected by the photosensor 24, i.e., the result of detecting whether there is a tissue obtained by the obtaining unit 23a. Specifically, the successful/unsuccessful determining unit 26a determines that the obtaining unit 23a succeeds in obtaining a tissue, when the successful/unsuccessful determining unit 26a does not receive a detection signal, which is obtained by converting the light from the light emitter 24a, in a predetermined time from when the light emitter 24a of the photosensor 24 emits the light. In contrast, when the successful/unsuccessful determining unit 26a receives a detection signal in the predetermined time, it determines that the obtaining unit 23a does not yet succeed in obtaining a tissue. When the successful/unsuccessful determining unit 26a determines that a tissue is successfully obtained, the control unit 26 sends successful/unsuccessful information representing that a tissue is successfully obtained to the communication unit 25, and controls the communication unit 25 to wirelessly transmit the successful/unsuccessful information to the outside. In contrast, when the successful/unsuccessful determining unit 26a determines that a tissue is unsuccessfully obtained, the control unit 26 sends the control signal for the series of obtaining operations to the drive unit 23b to cause the obtaining unit 23a to perform the series of obtaining operations again. In other words, the control unit 26 causes the biopsy mechanism 23 to repeatedly perform the series of obtaining operations until a tissue is successfully obtained.

The power unit 27 includes a switching circuit and a button-shaped battery. When the switching circuit switches on, the power unit 27 supplies power to the imaging unit 21, the signal processor 22, the biopsy mechanism 23, the photosensor 24, the communication unit 25, and the control unit 26.

The magnet 28 is, for example, a permanent magnet, an electromagnet, or a magnetic material. The magnet 28 is fixed in the cylindrical casing 20a such that, for example, the magnet 28 is magnetized in the direction perpendicular to the center axis CL shown in FIG. 2 in the longitudinal direction of the capsule casing 20 (i.e., the radial direction of the capsule casing 20). The magnet 28 moves in accordance with the external magnetic field formed by the magnetic-field generator 5 (see FIG. 1). Due to the action of the magnet 28, the capsule medical apparatus 2 is magnetically guided to a desired body site in the subject 1 to be in any posture, or pressed against the body site.

The capsule medical apparatus 2 having the above configuration is introduced into the subject 1 in the medical system 11 shown in FIG. 1. Thereafter, the capsule medical apparatus 2 captures a group of in-vivo images of the subject 1 while moving through the alimentary canal of the subject 1 due to peristalsis or the external magnetic field generated by the magnetic-field generator 5, and wirelessly transmits the group of in-vivo images to the outside. The display unit 4 outside the subject 1 displays the in-vivo images of the subject 1, which are captured by the capsule medical apparatus 2, and the current positional information about the capsule medical apparatus 2 in the subject 1. The user such as a doctor or a nurse refers to the information (the in-vivo images and the current positional information) displayed on the display unit 4 and operates the input unit 8 to guide the capsule medical apparatus 2 to the desired body site (the body site to be examined) in the subject 1. Specifically, the capsule medical apparatus 2 in the subject 1 is guided due to the external magnetic field generated by the magnetic-field generator 5, so that it reaches the body site to be examined. The user confirms the in-vivo images and the current position information displayed on the display unit 4 and determines whether the capsule medical apparatus 2 in the subject 1 reaches the body site to be examined.

When the capsule medical apparatus 2 in the subject 1 reaches the site to be examined, the user operates the input unit 8 while referring to the in-vivo images and the current positional information displayed on the display unit 4 to instruct the capsule medical apparatus 2 in the subject 1 to obtain a tissue. Based on instruction information input by the input unit, the control unit 10 outside the subject 1 generates a control signal (the control signal for the series of obtaining operations) to the capsule medical apparatus 2. The communication unit 3 transmits the control signal from the control unit 10 to the capsule medical apparatus 2 in the subject 1 via the antenna 3a.

The capsule medical apparatus 2 in the subject 1 performs the series of obtaining operations based on the control signal from the control unit 10, thereby obtaining a tissue from the body site to be examined. Thereafter, the capsule medical apparatus 2 then moves through the alimentary canal due to peristalsis or the external magnetic field, and is discharged to outside the subject 1 eventually. The tissue obtained by the capsule medical apparatus 2 is collected by, for example, a doctor or a nurse in order to perform a biopsy such as a pathological diagnosis.

Figure 4A:
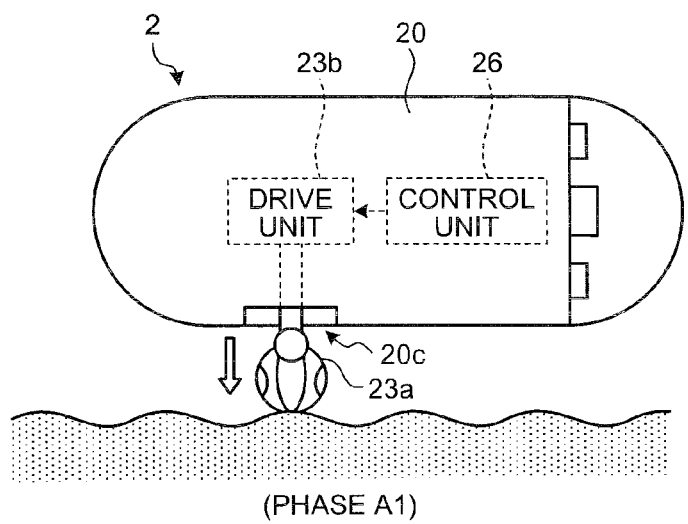
FIGS. 4A and 4B are schematic diagrams that show an example of phases where the obtaining unit of the capsule medical apparatus according to the first embodiment protrudes to a body site.
Figure 4B:
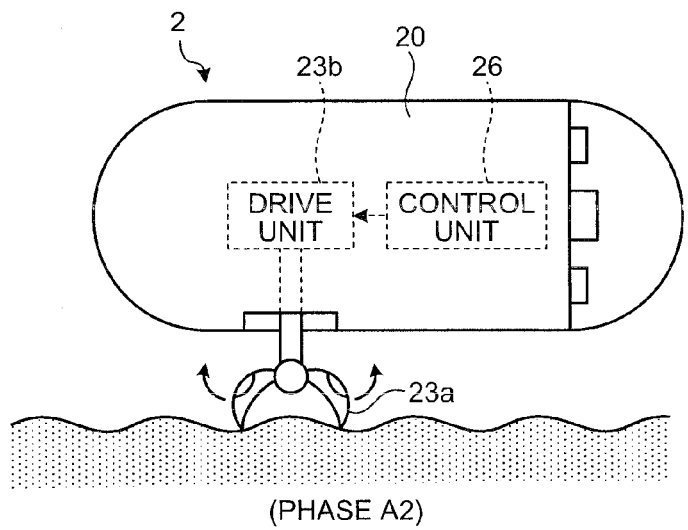
Figure 5A:
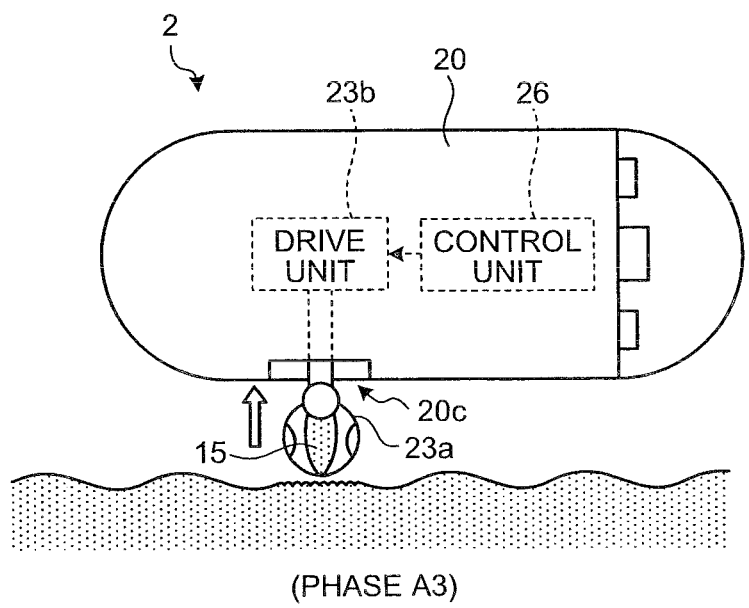
FIGS. 5A and 5B are schematic diagrams that show an example of phases where the obtaining unit of the capsule medical apparatus according to the first embodiment obtains a tissue from the body site.
Figure 5B:
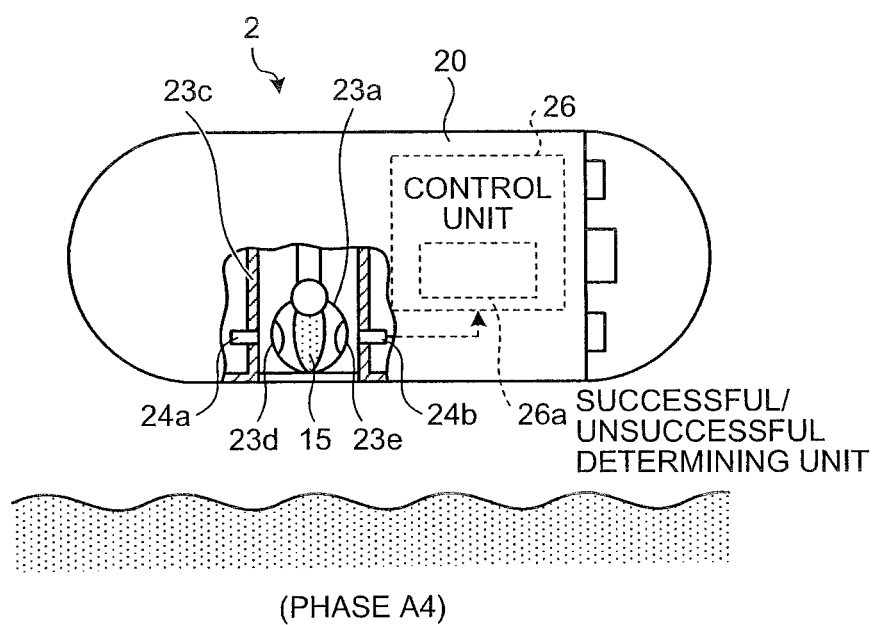

Operations of the capsule medical apparatus 2 for obtaining a tissue from a body site of the subject 1 are explained below. FIGS. 4A and 4B are schematic diagrams that show an example of phases where the obtaining unit 23a of the capsule medical apparatus 2 according to the first embodiment protrudes to a body site. FIGS. 5A and 5B are schematic diagrams that show an example of phases where the obtaining unit 23a of the capsule medical apparatus 2 according to the first embodiment obtains a tissue from the body site.

When the capsule medical apparatus 2 in the subject 1 reaches the body site to be examined (for example, a lesion in the alimentary canal such as the stomach, the small intestine, or the large intestine), it receives the control signal from the control unit 10 outside the subject 1. Based on the received control signal, the capsule medical apparatus 2 in the subject 1 performs the series of obtaining operations for obtaining a tissue from the body site. As shown in FIG. 4A, the capsule medical apparatus 2 protrudes the obtaining unit 23a from the opening 20c of the capsule casing 20. Specifically, based on the control signal from the control unit 10 outside the subject 1, the control unit 26 of the capsule medical apparatus 2 controls the drive unit 23b to cause the obtaining unit 23a to perform the series of obtaining operations. The obtaining unit 23a keeps protruding from the opening 20c of the capsule casing 20 toward the body site until it contacts with the body site (Phase 1).

Subsequently, the capsule medical apparatus 2 captures a part of the body site with the obtaining unit 23a that is caused to protrude as described above. Specifically, the drive unit 23b causes the forceps-shaped tips of the obtaining unit 23a to open while causing the obtaining unit 23a to protrude under the control by the control unit 26. The obtaining unit 23a captures a part of the body site with the opened forceps-shaped tips as shown in FIG. 4B (Phase A2).

The capsule medical apparatus 2 obtains a tissue from the body site with the obtaining unit 23a in the state of capturing a part of the body site. Specifically, the drive unit 23b causes the forceps-shaped tips of the obtaining unit 23a to close and then causes the closed obtaining unit 23a to move to the capsule casing 20 under the control by the control unit 26. As shown in FIG. 5A, the obtaining unit 23a excises an aggregated tissue 15 from the part of the body site captured with the forceps-shaped tips, thereby obtaining the tissue 15 (Phase A3). In Phase A3, the tissue 15 is held in the forceps-shaped tips of the obtaining unit 23a.

The capsule medical apparatus 2 then houses the obtaining unit 23a with the tissue 15 in the capsule casing 20. Specifically, as shown in FIG. 5B, the obtaining unit 23a is housed in the housing unit 23c while holding the tissue 15 (Phase A4). At this point, one cycle of the series of obtaining operations of the capsule medical apparatus 2 is completed. The tissue 15 is stored in the forceps-shaped tips of the obtaining unit 23a.

From when one cycle of the series of obtaining operations is started until it is completed, operation state information representing that the capsule medical apparatus 2 in the subject 1 is obtaining a tissue from the body site is displayed on the display unit 4. Specifically, the control unit 10 outside the subject 1 causes the communication unit 3 to wirelessly transmit the control signal to the capsule medical apparatus 2, and then, causes the display unit 4 to display the operation state information. The display unit 4 outputs and displays the operation state information of, for example, "OBTAINING TISSUE", under the control by the control unit 10. By seeing the operation state information displayed on the display unit 4, the user can easily know that that capsule medical apparatus 2 in the subject 1 is taking a tissue from the body site (i.e., performing the series of obtaining operations).

After the capsule medical apparatus 2 in the subject 1 completes one cycle of the series of obtaining operations, the control unit 26 causes the photosensor 24 to detect the state of the biopsy mechanism 23 (whether there is a tissue obtained by the obtaining unit 23a). Based on the result of the detection, the successful/unsuccessful determining unit 26a determines whether the obtaining unit 23a does not succeed in obtaining a tissue. As described above, the successful/unsuccessful determining unit 26a determines that a tissue is not obtained when it receives a detection signal from the light receiver 24b. In contrast, when the successful/unsuccessful determining unit 26a does not receive a detection signal from the light receiver 24b, it determines that the obtaining unit 23a succeeds in obtaining a tissue.

When the obtaining unit 23a successfully obtains the tissue 15 of the body site as shown in FIG. 5B, the light emitted by the light emitter 24a is blocked by the tissue 15 in the obtaining unit 23a, so that the light receiver 24b does not receive the light from the light emitter 24a. Thus, the light receiver 24b does not send a detection signal to the control unit 26, so that it is detected that there is the tissue 15 in the obtaining unit 23a. The successful/unsuccessful determining unit 26a does not receive a detection signal from the light receiver 24b and thus determines that the obtaining unit 23a succeeds in obtaining a tissue.

When the obtaining unit 23a succeeds in obtaining a tissue, the control unit 26 controls the communication unit 25 to wirelessly transmit successful/unsuccessful information representing that the obtaining unit 23a succeeds in obtaining the tissue 15, based on the determination result (representing that a tissue is successfully obtained) of the successful/unsuccessful determining unit 26a. The successful/unsuccessful information is received by the communication unit 3 outside the subject 1 and then received by the control unit 10 outside the subject 1 via the communication unit 3. The control unit 10 causes the display unit 4 to display the received successful/unsuccessful information. The display unit 4 outputs and displays message information of, for example, "OBTAINING TISSUE IS SUCCESSFUL", representing that a tissue is successfully obtained instead of the operation state information (information representing that the tissue obtained is being performed). By seeing the successful/unsuccessful information displayed on the display unit 4, the user can easily know that the capsule medical apparatus 2 in the subject 1 succeeds in obtaining a tissue from the body site, while the capsule medical apparatus 2 is still positioned in the body site (site to be examined) in the subject 1 before the capsule medical apparatus 2 is discharged or collected from the subject 1.

In contrast, when the obtaining unit 23a cannot obtain a tissue from the body site during one cycle of the series of obtaining operations, the light emitted by the light emitter 24a passes through the openings 23d and 23e sequentially, and the light emitter 24a receives the light from the light emitter 24a. The light receiver 24b then sends a detection signal, which is obtained by converting the light from the light emitter 24a, to the control unit 26. Thus, it is detected that there is no tissue in the obtaining unit 23a. The successful/unsuccessful determining unit 26a receives the detection signal from the light receiver 24b, and determines that the obtaining unit 23a does not succeed in obtaining a tissue based on the received detection signal.

When the obtaining unit 23a succeeds in obtaining a tissue, the control unit 26 causes the biopsy mechanism 23 to perform the series of obtaining operations again based on the determination result (representing that a tissue is not obtained) of the successful/unsuccessful determining unit 26a. In this case, the drive unit 23b causes the obtaining unit 23a to perform the series of obtaining operations again under the control by the control unit 26. The obtaining unit 23a performs one cycle of the series of obtaining operations (see Phases A1 to A4 shown in FIGS. 4A, 4B, 5A, and 5B) again due to the action of the drive unit 23b. The control unit 26 causes the obtaining unit 23a to repeatedly perform the series of obtaining operations until the obtaining unit 23a succeeds in obtaining a tissue.

As explained above, in the first embodiment of the present invention, the forceps-shaped obtaining unit configured to protrude from and retract into the capsule casing performs the series of obtaining operations for obtaining a tissue from a body site of a subject. The photosensor detects the state of the obtaining unit, which varies depending on whether a tissue is successfully obtained, i.e., whether there is a tissue obtained by the obtaining unit. The control unit determines whether the obtaining unit succeeds in obtaining a tissue based on the detection result of the photosensor, and causes the communication unit to transmit successful/unsuccessful information representing the successful/unsuccessful determination result to the outside. With this configuration, when a tissue is obtained from the body site of the subject, successful/unsuccessful information representing that a tissue is successfully obtained can be transmitted to outside the subject. This allows a user outside the subject to know the success in obtaining a tissue before the obtained tissue is taken out of the subject (collected). This leads to a capsule medical apparatus that allows a user to confirm whether a tissue is successfully obtained from a body site of a subject, while the capsule medical apparatus is still positioned in a desired body site in the subject.

The capsule medical apparatus according to the first embodiment is introduced into a subject to obtain a tissue from a body site. The communication unit outside the subject receives successful/unsuccessful information transmitted by the capsule medical apparatus in the subject, and the control unit outside the subject receives the successful/unsuccessful information via the communication unit and causes the display unit outside the subject to display the received successful/unsuccessful information. With this configuration, successful/unsuccessful information representing that a tissue is successfully obtained can be displayed, while the capsule medical apparatus is positioned in still a desired body site in the subject before it is discharged from the subject. This leads to a medical system that allows a user to easily confirm whether the capsule medical apparatus in the subject succeeds in obtaining a tissue from the body site when the capsule medical apparatus is still positioned in a desired body site in the subject.

When the obtaining unit does not succeed in obtaining a tissue, the control unit of the capsule medical apparatus causes the obtaining unit to perform the series of obtaining operations again. Therefore, the capsule medical apparatus in the subject can repeatedly perform the series of obtaining operations until a tissue is obtained from the body site without increasing operations of the user due to repetition of input operations. This makes input operations by the user less complicated, and assures that a tissue is obtained from the body site using the capsule medical apparatus in the subject.

A second embodiment of the present invention is explained below. In the first embodiment, the obtaining unit 23a in the forceps-like shape, which protrudes from or retracts into the capsule casing 20, obtains a tissue from a body site. In contrast, in the second embodiment, a part of a body site is sucked into a capsule casing and then a tissue is excised from the sucked part of the body site, thereby obtaining the tissue.

Figure 7:
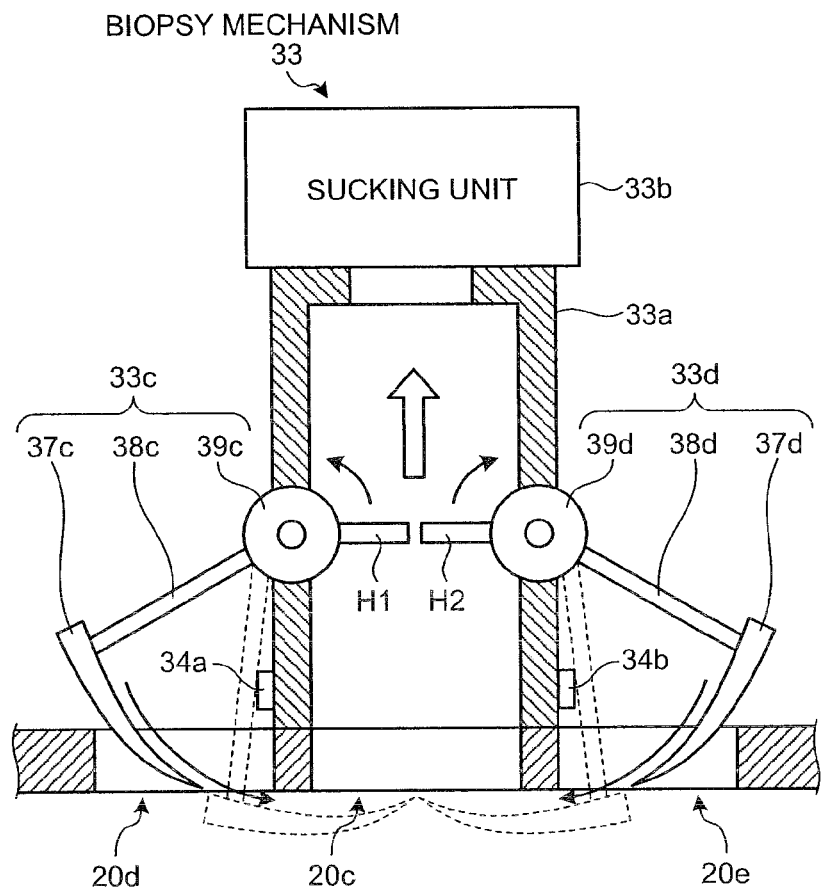
FIG. 7 is a schematic diagram of an enlarged view of a tissue obtaining unit of the capsule medical apparatus according to the second embodiment.

FIG. 6 is a schematic diagram of a configuration example of a capsule medical apparatus according to the second embodiment of the present invention. FIG. 7 is a schematic diagram of an enlarged view of a tissue obtaining unit of the capsule medical apparatus according to the second embodiment. As shown in FIGS. 6 and 7, a capsule medical apparatus 31 according to the second embodiment includes a biopsy mechanism 33 instead of the biopsy mechanism 23 of the capsule medical apparatus 2 according to the first embodiment. The capsule medical apparatus 31 further includes a pair of proximity sensors 34a and 34b instead of the photosensor 24, and includes a control unit 36 instead of the control unit 26. In the second embodiment, a pair of openings 20d and 20e for moving in or moving out a pair of excising units 33c and 33d of the biopsy mechanism 33 is formed in the cylindrical casing 20a of the capsule casing 20. The medical system according to the second embodiment includes the capsule medical apparatus 31 instead of the capsule medical apparatus 2 of the medical system 11 (see FIG. 1) according to the first embodiment. Other elements of the second embodiment are identical to those of the first embodiment, and the identical elements are denoted by the same reference numerals.

The biopsy mechanism 33 functions as a tissue obtaining unit that obtains a tissue from a body site of the subject 1, and it obtains a tissue by performing a series of obtaining operations under the control by the control unit 36. As shown in FIG. 7, the biopsy mechanism 33 includes a cylindrical housing unit 33a that houses therein a tissue from the body site of the subject 1, a sucking unit 33b, and the excising units 33c and 33d. The sucking unit 33b sucks a part of the body site into the housing unit 33a. The excising units 33c and 33d excise a tissue from the part of the body site, which is sucked into the housing unit 33a by the sucking unit 33b.

The housing unit 33a is a cylindrical member that stores therein a tissue from a body site, which is obtained by excision due to the action of the sucking unit 33b and the excising units 33c and 33d. The housing unit 33a is arranged near the opening 20c of the capsule casing 20. The housing unit 33a communicates with outside the capsule casing 20 via the opening 20c, and it partitions a space into an internal area of the capsule casing 20 in which electric devices, such as the control unit 36 and the power unit 27, are housed, and an area in which a tissue is housed.

The sucking unit 33b is, for example, a suction pump that operates under the control by the control unit 36. The sucking unit 33b sucks a part of the body site of the subject 1 into the housing unit 33a by suction in the direction indicted by the large arrow shown in FIG. 7. The suction pressure of the sucking unit 33b is large enough to suck a part of the body site to the back side in the housing unit 33a (i.e., near the sucking unit 33b).

The excising units 33c and 33d are arranged in the wall of the housing unit 33a such that they are rotatable and opposed to each other linearly. The excising units 33c and 33d operate due to the action of the part of the body site, which is sucked into the housing unit 33a by the sucking unit 33b, and excise an aggregated tissue from the part of the body site. The excising unit 33c includes a blade 37c for excising a tissue from the body site, a supporter 38c that supports the blade 37c, and a rotation shaft 39c that rotatably supports the supporter 38c. Similarly, the excising unit 33d includes a blade 37d for excising a tissue from the body site, a supporter 38d that supports the blade 37d, and a rotation shaft 39d that rotatably supports the supporter 38d.

The blade 37c is fixed to one end of the supporter 38c, and the blade 37d is fixed to one end of the supporter 38d. The blades 37c and 37d are positioned inside the capsule casing 20 in an initial state before a tissue is obtained. The blade 37c protrudes from the opening 20d to outside the capsule casing 20 while moving in the rotation direction of the supporter 38c that rotates on the center of the rotation shaft 39c. Similarly, the blade 37d protrudes from the opening 20e to outside the capsule casing 20 while moving in the rotation direction of the supporter 38d that rotates on the center of the rotation shaft 39d. The blades 37c and 37d protrude from the capsule casing 20 while generating an excision force that is sufficient to excise a tissue from the body site, and eventually move to a position where they close the opening 20c of the capsule casing 20. The blades 37c and 37d move to the position where they close the opening 20c and function as a cover of the housing unit 33a.

The supporters 38c and 38d are rotatably supported by the rotation shafts 39c and 39d, respectively. An end H1 of the supporter 38c is positioned inside the housing unit 33a and the other end supports the blade 37c. The end H1 of the supporter 38c is pushed and moved by the part of the body site, which is sucked into the housing unit 33a by the sucking unit 33b, and the supporter 38c rotates on the center of the rotation shaft 39c as the end H1 moves. In this case, as shown in FIG. 7, the supporter 38c rotates toward the housing unit 33a and causes the blade 37c to protrude to outside the capsule casing 20. Similarly, one end H2 of the supporter 38d is positioned inside the housing unit 33a, and the other end of the supporter 38d supports the blade 37d. The end H2 of the supporter 38d is pushed and moved by the part of the body site, which is sucked into the housing unit 33a by the sucking unit 33b, and the supporter 38d rotates on the center of the rotation shaft 39d as the end H2 moves. In this case, as shown in FIG. 7, the supporter 38d rotates toward the housing unit 33a, and causes the blade 37d to protrude to outside the capsule casing 20.

The rotation shafts 39c and 39d rotatably support the supporters 38c and 38d, and they are arranged in the wall of the housing unit 33a such that they are opposed to each other linearly. Specifically, the rotation shaft 39c rotatably supports the supporter 38 such that the part of the supporter 38c on the side of the blade 37c is positioned outside the housing unit 33a and the end H1 is positioned inside the housing unit 33a. Similarly, the rotation shaft 39d rotatably supports the supporter 38d such that the part of the supporter 38d on the side of the blade 37d is positioned outside the housing unit 33a and the end H2 is positioned inside the housing unit 33a.

The proximity sensors 34a and 34b function as a detecting unit that detects the state of the biopsy mechanism 33 that varies depending on whether the biopsy mechanism 33 succeeds in obtaining a tissue, for example, the position of a member of the biopsy mechanism 33 that vary with the series of obtaining operations of the biopsy mechanism 33. Specifically, the proximity sensor 34a is fixed in the position on the wall of the housing unit 33a to which the supporter 38c of the excising unit 33c is eventually adjacent due to its rotation. The proximity sensor 34a operates under the control by the control unit 36. When the supporter 38c is in a predetermined area (distance) from the proximity sensor 34a and adjacent to the proximity sensor 34a, the proximity sensor 34a detects the adjacent state of the supporter 38c (an example of the member position state). Similarly, the proximity sensor 34b is fixed in the position on the wall of the housing unit 33a to which the supporter 38d of the excising unit 33d is eventually adjacent due to its rotation. The proximity sensor 34b operates under the control by the control unit 36. When the supporter 38d is in a predetermined area (distance) from the proximity sensor 34b and adjacent to the proximity sensor 34b, the proximity sensor 34b detects the adjacent state of the supporter 38d (an example of the member position state). Detection results from the proximity sensors 34a and 34b are sent to the control unit 36.

The member position state of the biopsy mechanism 33 varies with the series of operations of the biopsy mechanism 33 as shown in the positions of the excising units 33c and 33d that operate to obtain a tissue from the body site. Specifically, before the series of obtaining operations are performed, the excising units 33c and 33d maintain the state where the blades 37c and 37d are positioned inside the capsule casing 20, i.e., the supporters 38c and 38d are separated from the housing unit 33a. Thereafter, the sucking unit 33b sucks a part of the body site into the housing unit 33a as an operation of the series of obtaining operations. The excising units 33c and 33d operate due to the action of the part of the body site, which is sucked into the housing unit 33a, and the blades 37c and 37d excise a tissue from the part of the body site, thereby obtaining the tissue. The obtained tissue is sucked into the housing unit 33a by the sucking unit 33b, and the series of obtaining operations of the biopsy mechanism 33 is completed. When the series of the obtaining operations of the biopsy mechanism 33 is successfully completed, the supporter 38c is then in the predetermined area and adjacent to the proximity sensor 34a and the supporter 38d is in the predetermined area and adjacent to the proximity sensor 34b. In other words, by detecting the adjacent states of the supporters 38d and 38d, it can be indirectly detected that the biopsy mechanism 33 successfully obtains a tissue.

The control unit 36 controls a sucking operation of the sucking unit 33b of the biopsy mechanism 33 instead of controlling the biopsy mechanism 23 according to the first embodiment. Specifically, the control unit 36 causes the sucking unit 33b of the biopsy mechanism 33 to start the sucking operation based on a control signal from the control unit 10 outside the subject 1 and perform the sucking operation until it succeeds in obtaining a tissue. The control unit 36 controls the sucking operation of the sucking unit 33b to control the series of obtaining operations of the biopsy mechanism 33. The control unit 36 controls the proximity sensors 34a and 34b instead of controlling the photosensor 24 according to the first embodiment.

The control unit 36 includes a successful/unsuccessful determining unit 36a instead of the successful/unsuccessful determining unit 26a of the capsule medical apparatus 2 according to the first embodiment. The successful/unsuccessful determining unit 36a determines whether a tissue is successfully obtained based on the member position state of the biopsy mechanism 33, which is detected by the proximity sensors 34a and 34b. Specifically, the successful/unsuccessful determining unit 36a receives results of detecting the adjacent state of the supporters 38c and 38d from the proximity sensors 34a and 34b, and determines that the biopsy mechanism 33 succeeds in obtaining a tissue based on the received detection results. In contrast, when the successful/unsuccessful determining unit 36a receives no detection results about the adjacent state of the supporters 38c and 38d from the proximity sensors 34a and 34b, it determines that the biopsy mechanism 33 does not succeed in obtaining a tissue.

Other functions of the control unit 36 are the same as those of the control unit 26 of the capsule medical apparatus 2 according to the first embodiment.

Figure 8:
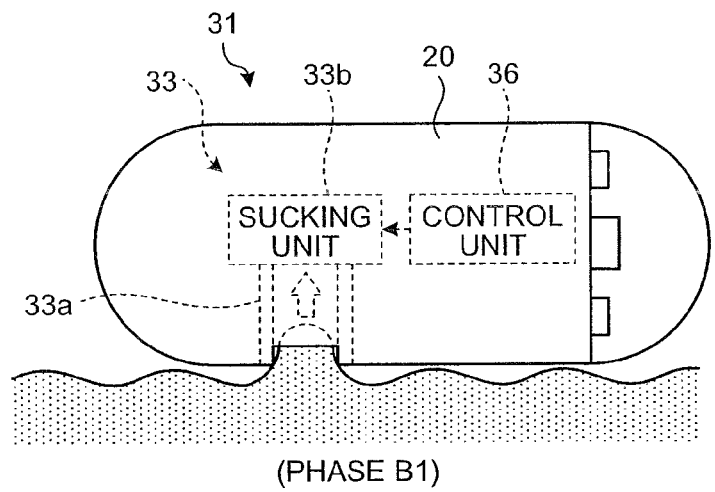
FIG. 8 is a schematic diagram that show an example of the phase where a biopsy mechanism of the capsule medical apparatus according to the second embodiment sucks a part of the body site.
Figure 9A:
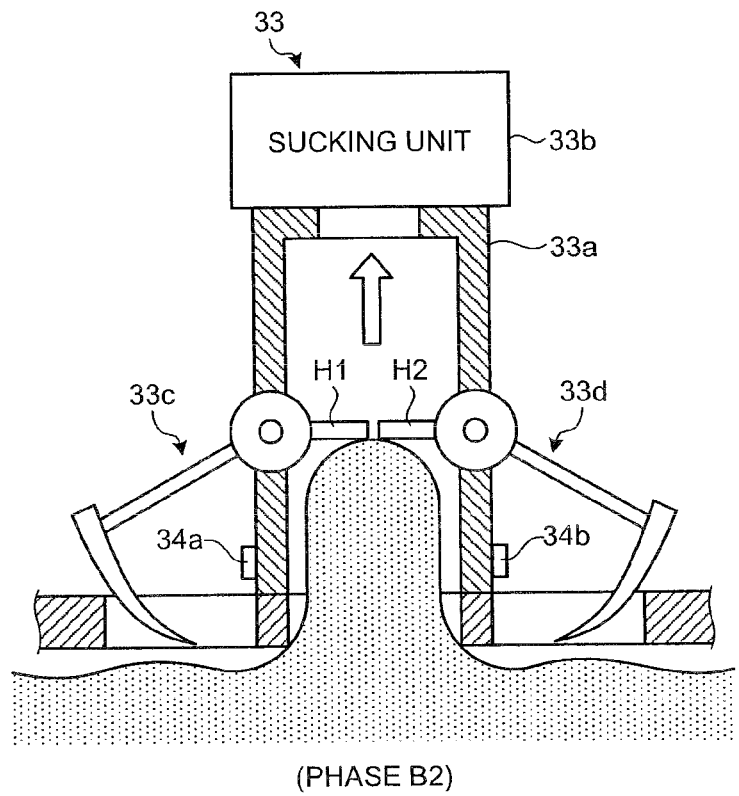
FIGS. 9A and 9B are schematic diagrams that show an example of phases where the biopsy mechanism of the capsule medical apparatus according to the second embodiment obtains a tissue from the body site.
Figure 9B:
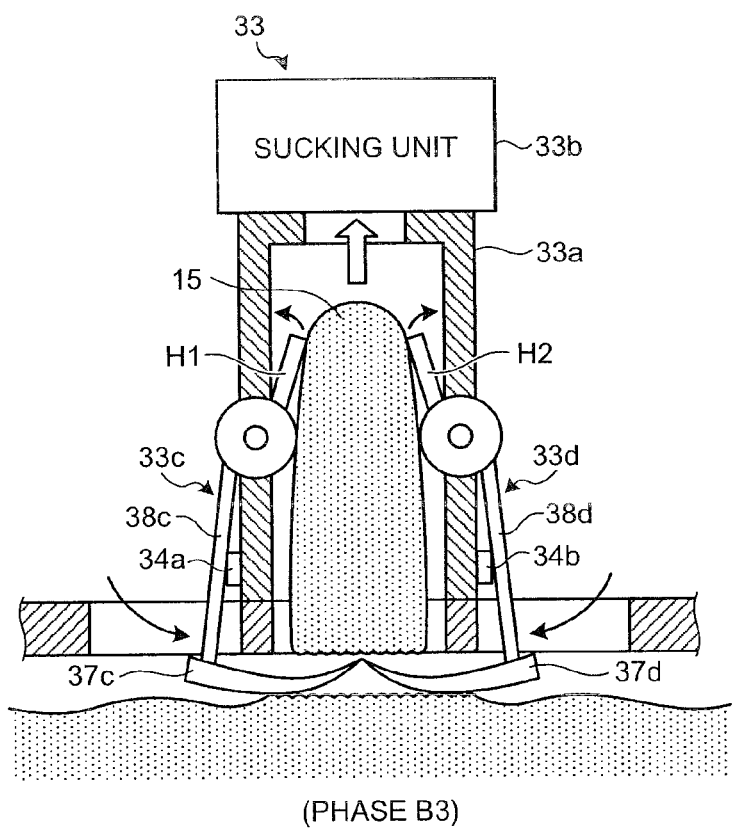

Operations of the capsule medical apparatus 31 for obtaining a tissue from a body site of the subject 1 are explained below. FIG. 8 is a schematic diagram that shows an example of the state where the biopsy mechanism 33 of the capsule medical apparatus 31 according to the second embodiment sucks a part of a body site. FIGS. 9A and 9B are schematic diagrams that show an example of the state where the biopsy mechanism 33 of the capsule medical apparatus 31 according to the second embodiment obtains a tissue from a body site.

After the capsule medical apparatus 31 is introduced into the subject 1, it reaches a body site to be examined in the subject 1. After the capsule medical apparatus 31 reaches the body site to be examined in the subject 1, it receives a control signal from the control unit outside the subject 1 and performs the series of obtaining operations for obtaining a tissue from the body site based on the received control signal.

As shown in FIG. 8, the capsule medical apparatus 31 first sucks a part of the body site into the capsule casing 20. Specifically, the control unit 36 of the capsule medical apparatus 31 controls driving of the sucking unit 33b based on the control signal from the control unit 10 outside the subject 1 to cause the biopsy mechanism 33 to perform the series of obtaining operations. The sucking unit 33b sucks a part of the body site into the housing unit 33a (Phase B1).

After the sucking unit 33b of the capsule medical apparatus 31 starts sucking a part of the body site, the biopsy mechanism 33 excises a tissue from the part of the body site as shown in FIG. 9A to obtain the tissue. Specifically, the sucking unit 33b keeps sucking the part of the body site into the housing unit 33a. As the part of the body site is sucked into the housing unit 33a, it contacts with the ends H1 and H2 of the excising units 33c and 33d (Phase B2).

Thereafter, as shown in FIG. 9B, the part of the body site is sucked into the back side in the housing unit 33a due to suction of the sucking unit 33b, and it pushes and moves the ends H1 and H2 of the excising units 33c and 33d. The excising units 33c and 33d cause the blades 37c and 37d to move toward the body site due to the action of the part of the body site, and the blades 37c and 37d excise the tissue 15 from the part of the body site, thereby obtaining the tissue 15 (Phase B3). The tissue 15 obtained by excision by the excising units 33c and 33d is sucked into the housing unit 33a by the sucking unit 33b and then stored in the housing unit 33a.

In Phase B3, the blades 37c and 37d close the opening of the housing unit 33a, which prevents the tissue 15 from spilling out of the inside of the housing unit 33a to outside the capsule casing 20. The supporters 38c and 38d that support the blades 37c and 37d are adjacent to the proximity sensors 34a and 34b, respectively in Phase B3.

In Phases B1 to B3, the control unit 36 of the capsule medical apparatus 31 causes the proximity sensors 34a and 34b to detect the state of the biopsy mechanism 33 (the member position state of the biopsy mechanism 33, which varies with the series of obtaining operations). Based on the detection results, the control unit 36 determines whether a tissue is successfully obtained. Specifically, as described above, the successful/unsuccessful determining unit 36a determines that the biopsy mechanism 33 succeeds in obtaining a tissue, when it receives detection results representing the adjacent state of the supporters 38c and 38d from the proximity sensors 34a and 34b. In contrast, when it receives no detection results representing the adjacent state of the supporters 38c and 38d from the proximity sensors 34a and 34b, the successful/unsuccessful determining unit 36a determines that the biopsy mechanism 33 does not succeed in obtaining a tissue.

When the biopsy mechanism 33 successfully obtains the tissue 15 from the body site as shown in FIG. 9B, the supporter 38c of the excising unit 33c is adjacent to the proximity sensor 34a and the proximity sensor 34a detects the adjacent state of the supporter 38c, and the supporter 38d of the excising unit 33d is adjacent to the proximity sensor 34b and the proximity sensor 34b detects the adjacent state of the supporter 38d. The detection results of the proximity sensors 34a and 34b are sent to the control unit 36. The successful/unsuccessful determining unit 36a receives the detection results from the proximity sensors 34a and 34b, and determines that the biopsy mechanism 33 succeeds in obtaining a tissue based on the received detection results. The control unit 36 then causes the sucking unit 33b to stop the sucking operation, and causes the biopsy mechanism 33 to complete the series of obtaining operations. The successful/unsuccessful information representing that the biopsy mechanism 33 succeeds in obtaining a tissue is displayed on the display unit 4 outside the subject 1 as in the case of the first embodiment.

In contrast, when the biopsy mechanism 33 does obtain a tissue from the body site yet, the supporter 38c of the excising unit 33c is separated from the proximity sensor 34a with a predetermined distance or more in between. Similarly, the supporter 38d of the excising unit 33d is separated from the proximity sensor 34b with a predetermined distance or more in between. Therefore, the proximity sensors 34a and 34b do not detect the adjacent state of the supporters 38c and 38d. In this case, the successful/unsuccessful determining unit 36a does not receive detection results from the proximity sensors 34a and 34b. Based on this fact, the successful/unsuccessful determining unit 36a determines that the biopsy mechanism 33 does not succeed in obtaining a tissue.

When the successful/unsuccessful determining unit 36a determines that the biopsy mechanism 33 does not succeed in obtaining a tissue, the sucking unit 33b of the sucking unit 33b is performing the sucking operation. In this case, based on the determination result (representing that a tissue is not obtained yet) of the successful/unsuccessful determining unit 36a, the control unit 36 causes the sucking unit 33b to continue performing the sucking operation. In other words, the control unit 36 causes the biopsy mechanism 33 to continue performing the series of obtaining operations until the biopsy mechanism 33 succeeds in sucking a tissue.

As explained above, in the second embodiment of the present invention, the biopsy mechanism performs the series of obtaining operations for obtaining a tissue by excising a tissue from a body site that is sucked into the housing unit by the sucking unit. The proximity sensors detect the member position state of the biopsy mechanism, which varies depending on whether a tissue is successfully obtained. The control unit determines whether the biopsy mechanism succeeds in obtaining a tissue based on the detection results of the proximity sensors, and causes the communication unit to transmit successful/unsuccessful information representing the determination result to outside the subject. Other elements of the second embodiment are identical to those of the first embodiment. Therefore, a user outside the subject can know that a tissue is successfully obtained, while the capsule medical apparatus is still positioned in a desired body site in the subject as in the case of the first embodiment. This leads to a capsules medical apparatus and a medical system that with the same functions and effects as those of the first embodiment.

The excising units of the biopsy mechanism that excise a tissue is operated using, as a drive source, a pressure of a part of a body site that is sucked into the housing unit by the sucking unit (i.e., suction pressure of the sucking unit) as a drive source, thereby obtaining the tissue. This reduces the power to drive the excising units, which reduces power consumption of the capsule medical apparatus that performs the series of obtaining operations.

Modification 1 of the second embodiment of the present invention is explained below. In the second embodiment, the proximity sensors 34a and 34b detect the member position state of the biopsy mechanism 33, which varies with the series of obtaining operation for obtaining a tissue by suction and excision, specifically, the adjacent state of the supporters 38c and 38d with respect to the housing unit 33a. Based on the detection results from the proximity sensors 34a and 34b, it is determined whether a tissue is successfully obtained. In contrast, in Modification 1 of the second embodiment, a pressure sensor detects a suction pressure of the sucking unit 33b that varies with the series of obtaining operations, and it is determined whether a tissue is successfully obtained based on the detection result of the pressure sensor.

Figure 10:
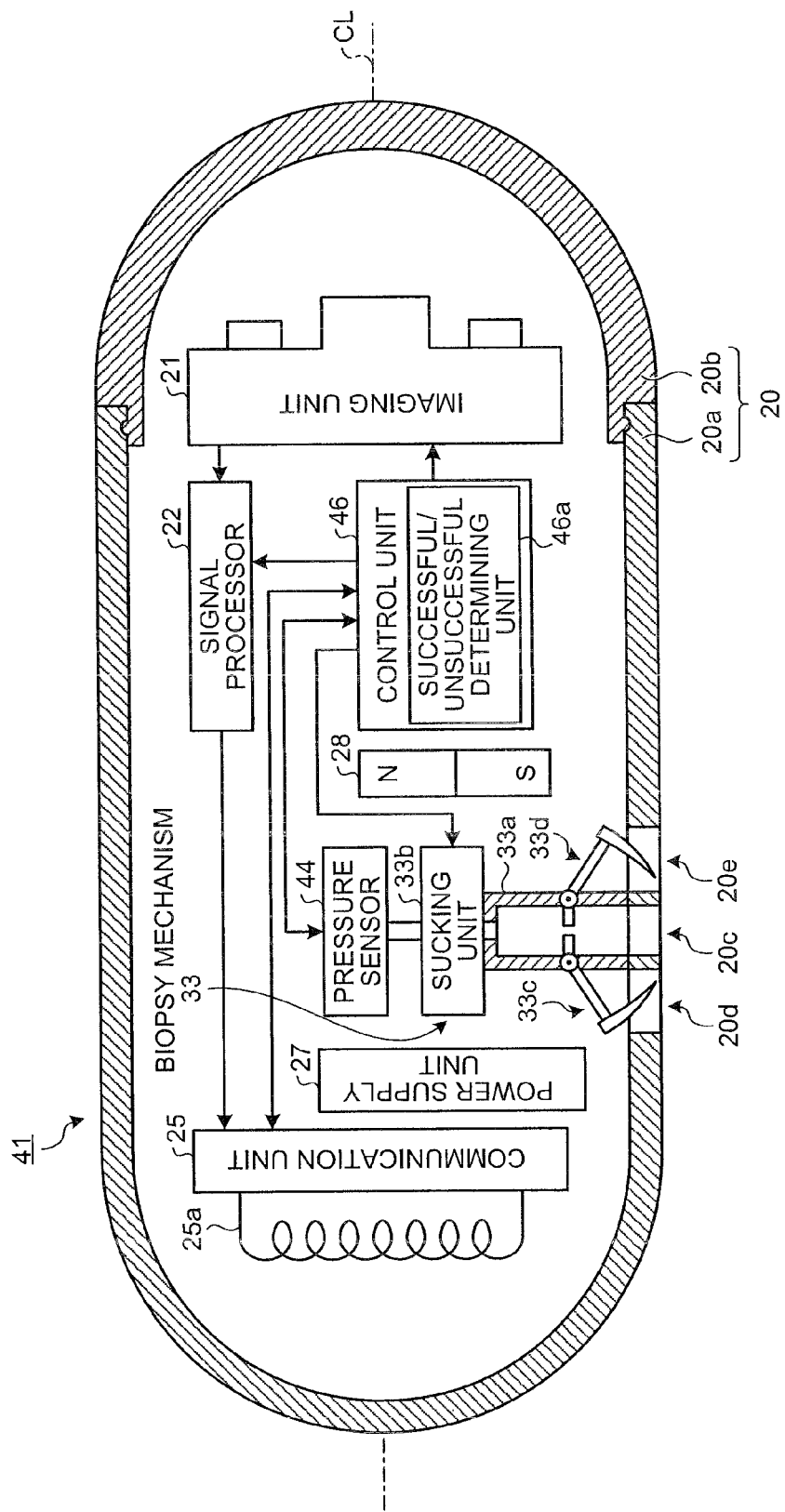
FIG. 10 is a schematic diagram of a configuration example of a capsule medical apparatus of Modification 1 of the second embodiment.

FIG. 10 is a schematic diagram of a configuration example of the capsule medical apparatus according to Modification 1 of the second embodiment. As shown in FIG. 10, a capsule medical apparatus 41 according to Modification 1 of the second embodiment includes a pressure sensor 44 instead of the proximity sensors 34a and 34b of the capsule medical apparatus 31 according to the second embodiment, and includes a control unit 46 instead of the control unit 36. The medical system according to Modification 1 of the second embodiment includes the capsule medical apparatus 41 instead of the capsule medical apparatus 31 according to the second embodiment. Other elements of Modification 1 are identical to those of the second embodiment, and the identical elements are denoted by the same reference numerals.

The pressure sensor 44 functions as a detecting unit that detects the state of the biopsy mechanism 33 that varies depending on whether the biopsy mechanism 33 succeeds in obtaining a tissue, for example, a suction pressure of the sucking unit 33b that varies with the series of obtaining operations of the biopsy mechanism 33. Specifically, the pressure sensor 44 detects the suction pressure of the sucking unit 33b under the control by the control unit 46 while the sucking unit 33b performs the sucking operations, and sends a result of detecting the suction pressure to the control unit 46.

The control unit 46 controls the pressure sensor 44 instead of controlling the proximity sensors 34a and 34b according to the second embodiment. Specifically, the control unit 46 causes the pressure sensor 44 to start a detecting operation for detecting the suction pressure of the sucking unit 33b at timing when the control unit 46 causes the sucking unit 33b to start the sucking operation. While the control unit 46 causes the sucking unit 33b to perform the sucking operations, the control unit 46 controls the pressure sensor 44 to continuously or intermittently detect the suction pressure of the sucking unit 33b and sequentially receive results of detecting the suction pressure from the pressure sensor 44 chronologically.

The control unit 46 includes a successful/unsuccessful determining unit 46a instead of the successful/unsuccessful determining unit 36a of the capsule medical apparatus 31 according to the second embodiment. The successful/unsuccessful determining unit 46a determines whether a tissue is successfully obtained based on the suction pressure of the sucking unit 33b, which varies with the series of obtaining operations of the biopsy mechanism 33. Specifically, the successful/unsuccessful determining unit 46a sequentially receives the results of detecting the suction pressure of the sucking unit 33b from the pressure sensor 44, thereby acquiring chronological variations in the suction pressure of the sucking unit 33b. The successful/unsuccessful determining unit 46a determines whether a tissue is successfully obtained based on the chronological variations in the suction pressure of the sucking unit 33b. Other functions of the control unit 46 are the same as those of the control unit 36b of the capsule medical apparatus 31 according to the second embodiment.

Figure 11:
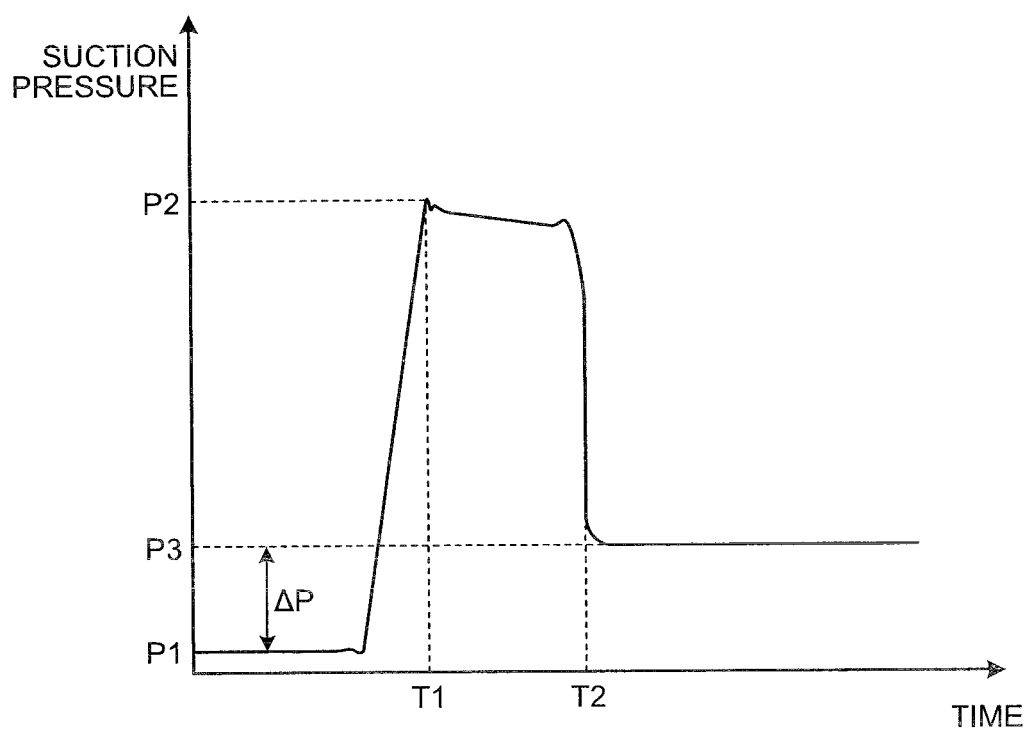
FIG. 11 is a schematic diagram that shows an example of chronological variations in the suction pressure of a suction unit that a pressure sensor detects.

The process for determining whether a tissue is successfully obtained that is performed by the successful/unsuccessful determining unit 46a is explained in detail below. FIG. 11 is a schematic diagram that shows an example of chronological variations in the suction pressure of the sucking unit 33b that is detected by the pressure sensor 44. The pressure sensor 44 sequentially detects the suction pressure of the sucking unit 33b that varies chronologically as shown in FIG. 11. The successful/unsuccessful determining unit 46a determines whether a tissue is successfully obtained based on the chronological variations in the suction pressure of the sucking unit 33b, which is detected by the pressure sensor 44.

Specifically, as shown in FIG. 11, the pressure sensor 44 detects a suction pressure P1 (minimum value) of the sucking unit 33b from when the sucking unit 33b starts the sucking operation until it starts sucking a part of a body site into the housing unit 33a. Thereafter, the suction pressure of the sucking unit 33b, which is detected by the pressure sensor 44, increases as that part of the body site is sucked into the housing unit 33a. The pressure sensor 44 detects a suction pressure P2 (maximum value) of the sucking unit 33b at timing (time T1) at which the opening 20c of the capsule casing 20 is closed with the part of the body site sucked into the housing unit 33a. Thereafter, the suction pressure detected by the pressure sensor 44 is approximately equal to the suction pressure P2 until a tissue is excised from the part of the body site, which is sucked into the housing unit 33a. The suction pressure then drops at timing (time T2) at which a tissue is excised from the part of the body site in the housing unit 33a. At the time T2, the pressure sensor 44 detects a suction pressure P3 of the sucking unit 33b. Thereafter, the suction pressure of the sucking unit 33b detected by the pressure sensor 44 is approximately equal to the suction pressure P3.

The successful/unsuccessful determining unit 46a sequentially receives the sucking pressure (for example, the suction pressures P1 to P3 shown in FIG. 11) of the sucking unit 33b, which is detected by the pressure sensor 44, chronologically. Based on the chronological variations in the received sucking pressure, the successful/unsuccessful determining unit 46a determines whether a tissue is successfully obtained. Specifically, the successful/unsuccessful determining unit 46a selects the initial suction pressure P1 and the suction pressure P3 obtained after the suction pressure drops from the suction pressure P2 (maximum value). The successful/unsuccessful determining unit 46a calculates a pressure difference ΔP between the suction pressure P3 and the suction pressure P1. The successful/unsuccessful determining unit 46a then compares the pressure difference ΔP with a predetermined threshold, and determines whether a tissue is successfully obtained based on the result of the comparison.

When the biopsy mechanism 33 succeeds in obtaining a tissue, the tissue obtained by excision is stored in the housing unit 33a. Therefore, the suction pressure P3 is larger than the initial suction pressure P1, and the pressure difference ΔP between the suction pressure P3 and the suction pressure P1 is larger than the threshold. In contrast, when the biopsy mechanism 33 does not succeed in obtaining a tissue, no tissue is sucked into the housing unit 33a. Therefore, the suction pressure P3 is approximately equal to the suction pressure P1, and the pressure difference ΔP between the suction pressure P3 and the suction pressure P1 is smaller than the threshold (approximately 0). As explained above, the successful/unsuccessful determining unit 46a determines that the biopsy mechanism 33 succeeds in obtaining a tissue when the pressure difference ΔP is equal to or larger than the threshold, or determines that the biopsy mechanism 33 does not succeed in obtaining a tissue when the difference ΔP is smaller than the threshold.

As explained above, in Modification 1 of the second embodiment of the present invention, the pressure sensor detects the suction pressure of the biopsy mechanism, which varies depending on whether a tissue is successfully obtained. The control unit determines whether the biopsy mechanism succeeds in obtaining a tissue based on variations in the suction pressure, which is detected by the pressure sensor, instead of the detection results of the proximity sensors. Other elements of Modification 1 are identical to those of the second embodiment. Therefore, a user outside the subject can know that a tissue is successfully obtained, while the capsule medical apparatus is still positioned in a desired body site in the subject, as in the case of the second embodiment. This leads to a capsule medical apparatus and a medical system with the same functions and effects as those of the second embodiment.

Modification 2 of the second embodiment of the present invention is explained below. In the second embodiment, the proximity sensors 34a and 34b detect the member position state of the biopsy mechanism 33, which varies with the series of obtaining operations for obtaining a tissue by suction and excision, specifically, the adjacent state of the supporters 38c and 38d with respect to the housing unit 33a. Based on the detection results from the proximity sensors 34a and 34b, it is determines whether a tissue is successfully obtained. In contrast, in Modification 2 of the second embodiment, a pair of electrodes is provided on the inner wall of the housing unit 33a that houses therein a tissue sucked by the sucking unit 33b. Based on an electric resistance between the electrodes, it is determined whether a tissue is successfully obtained.

Figure 12:
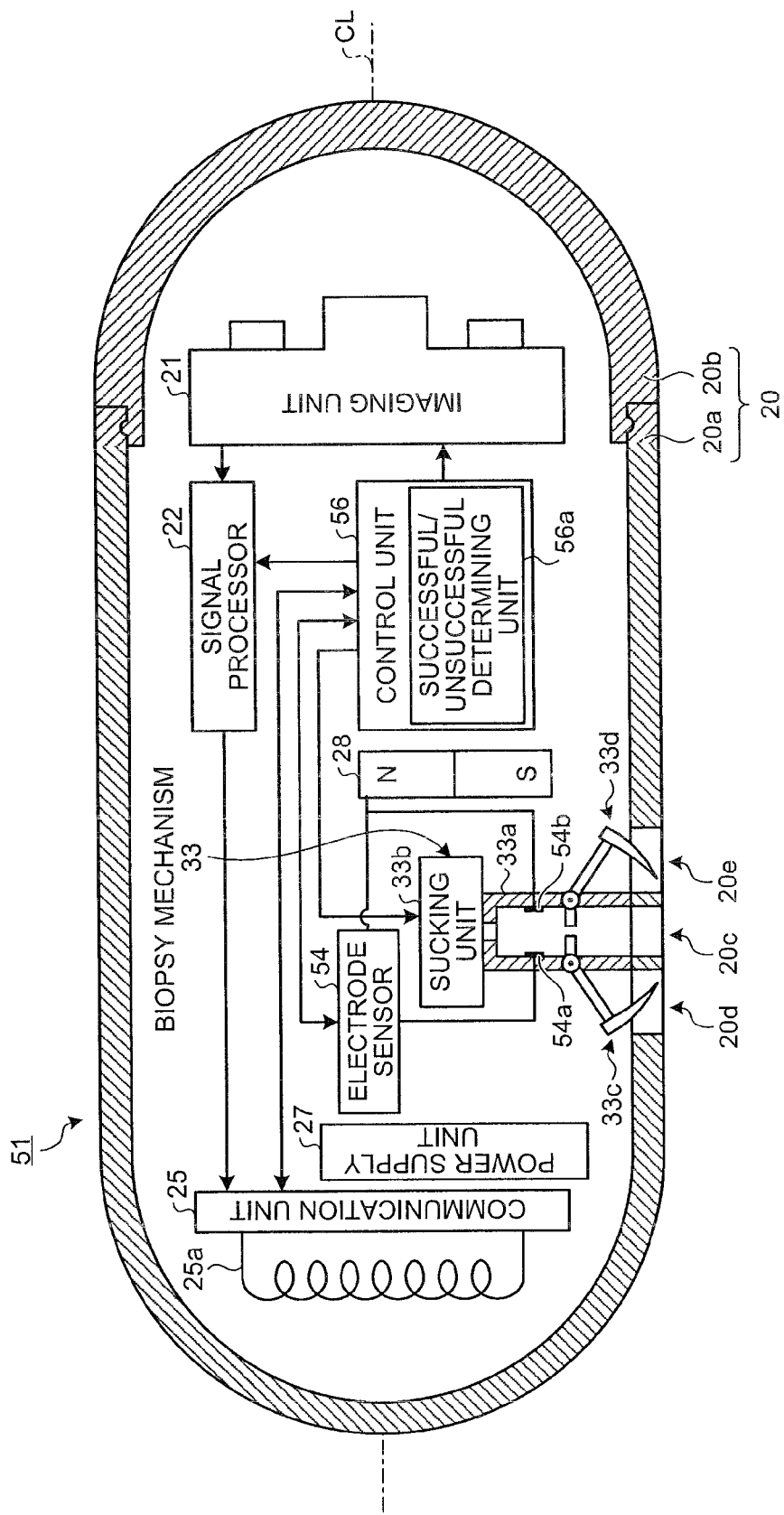
FIG. 12 is a schematic diagram of a configuration example of a capsule medical apparatus according to Modification 2 of the second embodiment.

FIG. 12 is a schematic diagram of a configuration example of a capsule medical apparatus according to Modification 2 of the second embodiment of the present invention. As shown in FIG. 12, a capsule medical apparatus 51 according to Modification 2 of the second embodiment includes a pair of electrodes 54a and 54b on the inner wall of the housing unit 33a that is formed of an insulating member. The capsule medical apparatus 51 further includes an electrode sensor 54 that detects an eclectic resistance between the electrodes 54a and 54b, instead of the proximity sensors 34a and 34b of the capsule medical apparatus 31 according to the second embodiment, and includes a control unit 56 instead of the control unit 36. The medical system according to Modification 2 of the embodiment 2 includes the capsule medical apparatus 51 instead of the capsule medical apparatus 31 of the medical system according to the second embodiment. Other elements of Modification 2 are identical to those of the second embodiment, and the identical elements are denoted by the same reference numerals.

The electrode sensor 54 functions as a detecting unit that detects the state of the biopsy mechanism 33 that varies depending on whether the biopsy mechanism 33 succeeds in obtaining a tissue, for example, an electric resistance that varies depending on whether there is a tissue obtained by the biopsy mechanism 33. Specifically, the electrode sensor 54 is electrically connected to the electrodes 54a and 54b provided on the inner wall of the housing unit 33a, and it detects the electric resistance between the electrodes 54a and 54b under the control by the control unit 56, and sends a result of detecting the electric resistance to the control unit 56. The electrodes 54a and 54b are electrically insulated when there is no tissue in the housing unit 33a. When there is a tissue in the housing unit 33a, i.e., when the biopsy mechanism 33 succeeds in obtaining a tissue, the electrodes 54a and 54b are electrically conductive via the tissue in the housing unit 33a.

The control unit 56 controls the electrode sensor 54 instead of controlling the proximity sensors 34a and 34b according to the second embodiment. Specifically, the control unit 56 causes the electrode sensor 54 to perform the detection operation for detecting the electric resistance between the electrodes 54a and 54b at timing at which the control unit 56 causes the biopsy mechanism 33 to start the series of obtaining operations (i.e., timing at which the control unit 56 causes the sucking unit 33b to start the sucking operation). The control unit 56 controls the electrode sensor 54 to continuously or intermittently detect the electric resistance between the electrodes 54a and 54b, and sequentially receives results of detecting the electric resistance from the electrode sensor 54, while the control unit 56 causes the biopsy mechanisms 33 to perform the series of obtaining operations.

The control unit 56 includes a successful/unsuccessful determining unit 56a instead of the successful/unsuccessful determining unit 36a. The successful/unsuccessful determining unit 56a determines whether a tissue is successfully obtained based on the electric resistance that varies depending on whether there is a tissue obtained by the biopsy mechanism 33. Specifically, the successful/unsuccessful determining unit 56a sequentially receives results of detecting the electric resistance between the electrodes 54a and 54b from the electrode sensor 54, and performs a comparing process for comparing the received eclectic resistance with a predetermined threshold. Based on a result of the comparing process, the successful/unsuccessful determining unit 56a determines whether a tissue is successfully obtained. Other functions of the control unit 56 are the same as those of the control unit 36 of the capsule medical apparatus 31 according to the second embodiment.

When the biopsy mechanism 33 succeeds in obtaining a tissue, the tissue excised by the excising units 33c and 33d is stored in the housing unit 33a and the electrodes 54a and 54b are electrically conductive with the tissue. In this case, the electric resistance between the electrodes 54a and 54b drops to a value smaller than a threshold that is preset in the successful/unsuccessful determining unit 56a. In contrast, when the biopsy mechanism 33 does not succeed in obtaining a tissue, the electrodes 54a and 54b are insulated because no tissue is housed in the housing unit 33a. In this case, the electric resistance between the electrodes 54a and 54b is equal to or larger than the threshold set in the successful/unsuccessful determining unit 56a. The successful/unsuccessful determining unit 56a determines that the biopsy mechanism 33 succeeds in obtaining a tissue when the electric resistance between the electrodes 54a and 54b is smaller than the threshold. In contrast, when the electric resistance between the electrodes 54a and 54b is equal to or larger than the threshold, the successful/unsuccessful determining unit 56a determines that the biopsy mechanism 33 does not succeed in obtaining a tissue.

As explained above, in Modification 2 of the second embodiment of the present invention, a pair of electrodes is provided on the inner wall of the housing unit in which a tissue obtained by excision is stored. The electrode sensor detects the electric resistance between the electrodes that varies depending on whether a tissue is successfully obtained. The control unit determines whether the biopsy mechanism succeeds in obtaining a tissue based on the electric resistance detected by the electrode sensor, instead of the detection results from the proximity sensors. Other elements of Modification 2 are identical to those of the second embodiment. With the above configuration, a user outside a subject can know that a tissue is successfully obtained, while the capsule medical apparatus is still positioned in a desired body site in the subject, as in the case of the second embodiment. This leads to a capsule medical apparatus and a medical system with the same functions and effects as those of the second embodiment.

A third embodiment of the present invention is explained below. In the first embodiment, when the capsule medical apparatus 2 in the subject 1 successfully obtains a tissue from a body site, the successful/unsuccessful information representing that a tissue is successfully obtained is displayed on the display unit 4 outside the subject 1. In contrast, in the third embodiment, operation sate information representing a progress of the series of obtaining operations of the capsule medical apparatus in the subject 1 is displayed on the display unit 4 before the successful/unsuccessful information is displayed on the display unit 4.

Figure 13:
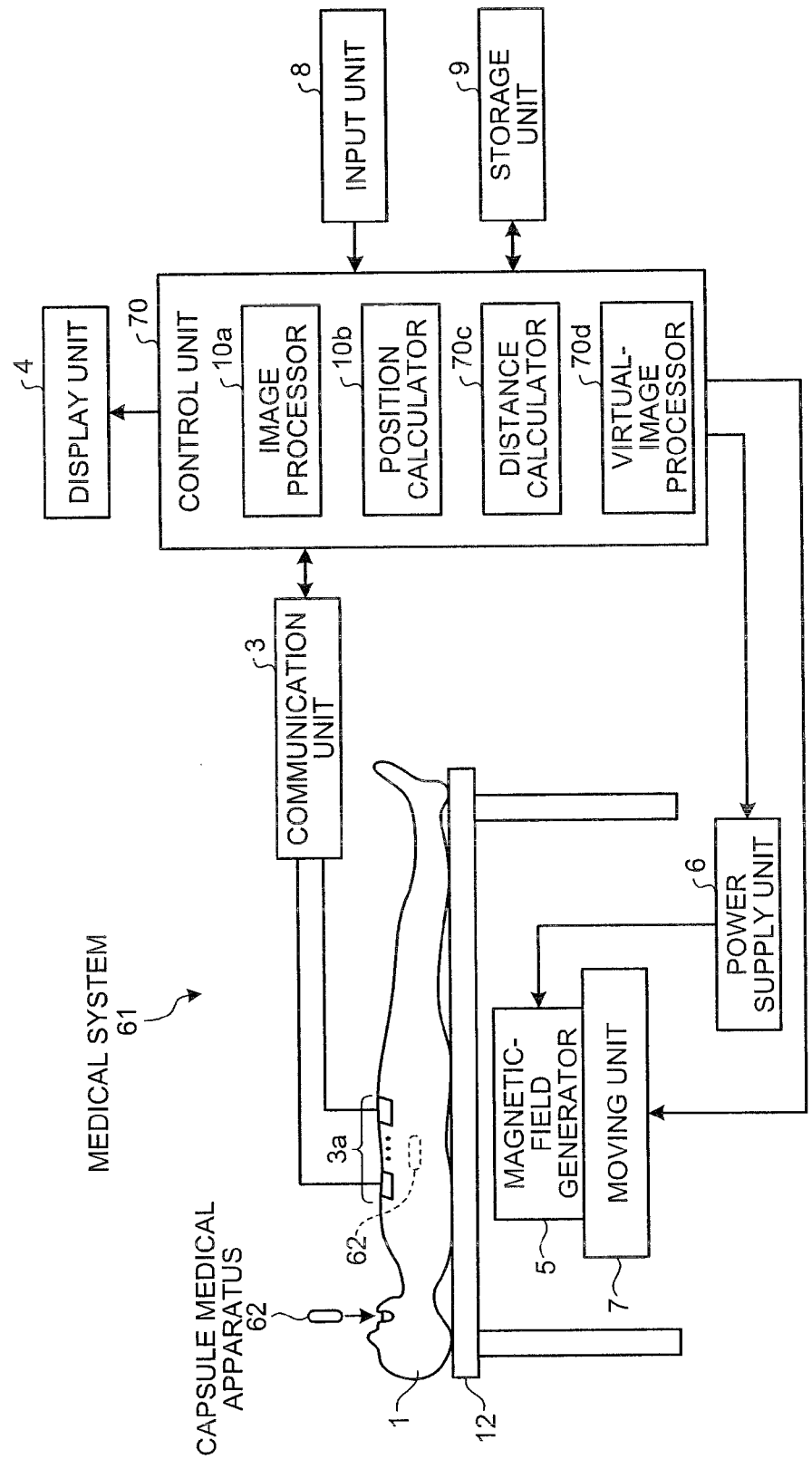
FIG. 13 is a block diagram that schematically represents a configuration example of a medical system according to a third embodiment of the present invention.

FIG. 13 is a block diagram that schematically shows a configuration example of a medical system according to the third embodiment of the present invention. As shown in FIG. 13, a medical system 61 according to the third embodiment includes a capsule medical apparatus 62 instead of the capsule medical apparatus 2 of the medical system 11 according to the first embodiment, and includes a control unit 70 instead of the control unit 10. Other elements of the third embodiment are identical to those of the first embodiment, and the identical elements are denoted by the same reference numerals.

The capsule medical apparatus 62 detects a progress of the series of obtaining operations while the series of obtaining operations for obtaining a tissue from a body site of the subject 1 are performed. Each time a progress is detected, the capsule medical apparatus 62 wirelessly transmits operation state information representing the detected progress. Other functions of the capsule medical apparatus 62 are the same as those of the capsule medical apparatus 2 according to the first embodiment. The capsule medical apparatus 62 according to the third embodiment is explained in detail below.

The control unit 70 has the same functions as those of the control unit 10 of the medical system 11 according to the first embodiment. The control unit 70 has a position control function of calculating a distance between the capsule medical apparatus 62 in the subject 1 and a target site in the subject 1 and controlling adjustment of the positions of the capsule medical apparatus 62 and the target site with high accuracy based on the calculated distance. The control unit 70 also has a display control function of generating virtual images representing the progress of the series of obtaining operations that the capsule medical apparatus 62 is performing and causing the display unit 4 to display the generated virtual images. The control unit 70 includes the image processor 10a and the position calculator 10b, and further includes a distance calculator 70c and a virtual-image processor 70d.

The distance calculator 70c calculates a distance between a target site, such as a lesion, and the capsule medical apparatus 62 in the subject 1 based on in-vivo images of the subject 1 that are captured by the capsule medical apparatus 62 and position information that is specified and input in an in-vivo image by the input unit 8. The control unit 70 controls the magnetic direction of the electric-field generator 5 or the position of the moving unit 7 based on the distance calculated by the distance calculator 70c, to adjust the position of the body site (for example, a target site such as a lesion), which is input by the input unit 8, and the position of the capsule medical apparatus 62 with high accuracy.

The virtual-image processor 70d receives the operation state information from the capsule medical apparatus 62 in the subject 1 via the communication unit 3, and generates virtual images representing the progress of the series of obtaining operations corresponding to the operation state information. The control unit 70 sets the operation mode to a normal mode or a virtual mode based on instruction information input by the input unit 8. In the normal mode, the control unit 70 causes the display unit 4 to display the in-vivo images of the subject 1. In the virtual mode, the control unit 70 causes the display unit 4 to display the virtual images generated by the virtual-image processor 70d.

Figure 14:
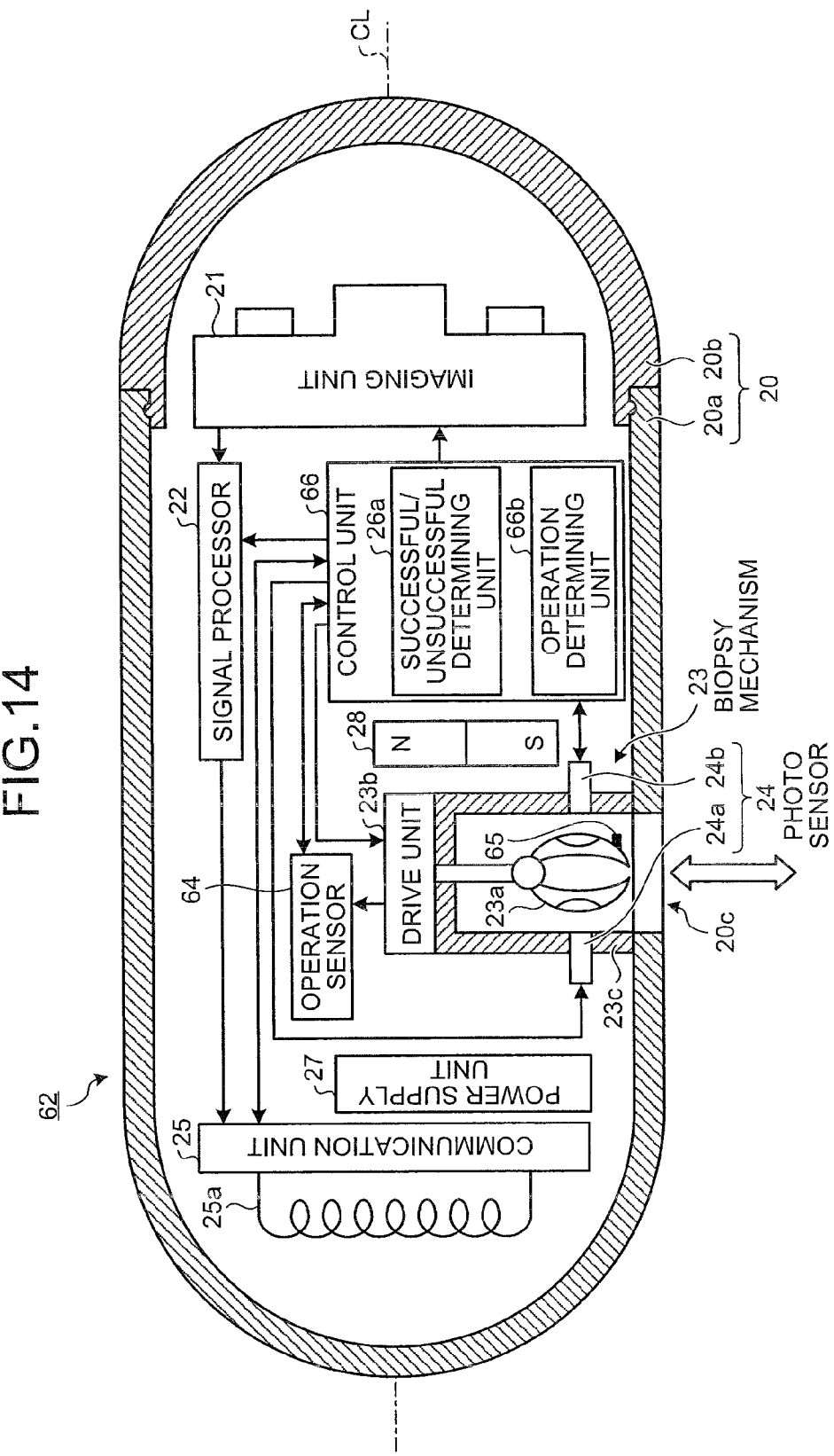
FIG. 14 is a schematic diagram of a configuration example of a capsule medical apparatus according to the third embodiment.

A configuration of the capsule medical apparatus 62 according to the third embodiment of the present invention is explained in detail below. FIG. 14 is a schematic diagram of a configuration example of the capsule medical apparatus according to the third embodiment of the present invention. As shown in FIG. 14, the capsule medical apparatus 62 according to the third embodiment includes a plurality of detecting units that detect a progress of the series of obtaining operations of the biopsy mechanism 23. Specifically, the capsule medical apparatus 62 includes an operation sensor 64 and a contact sensor 65, and includes a control unit 66 instead of the control unit 26 of the capsule medical apparatus 2 according to the first embodiment. Other elements of the third embodiment are identical to those of the first embodiment, and the identical elements are denoted by the same reference numerals.

The operation sensor 64 is one of the detecting units that detect a progress of the series of obtaining operations of the biopsy mechanism 23. Specifically, the operation sensor 64 sequentially detects the operation state of the drive unit 23b of the biopsy mechanism 23 chronologically under the control by the control unit 66, thereby detecting a progress of operations of the obtaining unit 23a during the series of obtaining operations. The progress of the operations of the obtaining unit 23a, which is detected by the operation sensor 64, is for example, a distance that the obtaining unit 23a, which protrudes from or retracts into the capsule casing 20, moves during the series of the obtaining operations, or an open/close state of the forceps-shaped tips of the obtaining unit 23a. In other words, the operation sensor 64 has a function of a distance sensor that detects a distance that the obtaining unit 23a moves during the series of obtaining operations. The operation sensor 64 sends a result of detecting the progress of the operations of the obtaining unit 23a to the control unit 66.

The contact sensor 65 is one of the detecting units that detect the progress of the series of obtaining operations of the biopsy mechanism 23. Specifically, the contact sensor 65 is arranged on the forceps-shaped tips of the obtaining unit 23a and connected to the control unit 66 via the obtaining unit 23a, the drive unit 23b, and the operation sensor 64. The contact sensor 65 detects that the obtaining unit 23a and a tissue from the body site contact with each other under the control by the control unit 66, and sends a result of the detection to the control unit 66 via the operation sensor 64.

While the control unit 66 causes the biopsy mechanism 23 to perform the series of obtaining operations, the control unit 66 controls the operation sensor 64 and the contact sensor 65 and receives detection results from the operation sensor 64 and the contact sensor 65. Specifically, the control unit 66 causes the operation sensor 64 and the contact sensor 65 to start the detection operation at the timing at which the control unit 66 causes the biopsy mechanism 23 to start the series of obtaining operations. The control unit 66 continuously or intermittently receives the detection results from the operation sensor 64 chronologically, and receives the detection result from the contact sensor 65 when a tissue from the body site contacts with the obtaining unit 23a.

The control unit 66 further includes an operation determining unit 66b that determines the progress of the series of obtaining operations of the biopsy mechanism 23. The operation determining unit 66b receives a detection result from the operation sensor 64 or the contact sensor 65, and determines the progress of the series of obtaining operations of the biopsy mechanism 23 based on the received detection result (representing the progress of the operations of the obtaining unit 23a during the series of obtaining operations, or the obtaining unit 23a contacts with a tissue from the body site). Specifically, the operation determining unit 66b determines how much the obtaining unit 23a moves during the series of obtaining operations, based on the distance the obtaining unit 23a moves which is detected by the operation sensor 64. The operation determining unit 66b determines whether the forceps-shaped tips of the obtaining unit 23a open or close, based on the open/close state detected by the operation sensor 64. The operation determining unit 66b determines that the obtaining unit 23a protruding from the capsule casing 20 contacts with a tissue from the body site, based on the detection result from the contact sensor 65. Each time the operation determining unit 66b determines the progress of the series of obtaining operations, the control unit 66 sends operation state information representing the result of the determination by the operation determining unit 66b to the communication unit 25. The control unit 66 controls the communication unit 25 to wirelessly transmit the operation state information to the outside. Other functions of the control unit 66 are the same as those of the control unit 26 of the capsule medical apparatus 2 according to the first embodiment.

In the medical system 61 shown in FIG. 13, the capsule medical apparatus 62 having the above configuration performs the series of obtaining operations based on a control signal from the control unit 70 outside the subject 1 to obtain a tissue from a desired body site as in the case of the first embodiment. The capsule medical apparatus 62 performs the series of obtaining operations and wirelessly transmits the operation state information representing the progress of the series of obtaining operations sequentially to the communication unit 3 outside the subject 1. Each time the control unit 70 receives the operation state information from the capsule medical apparatus 62, the control unit 70 then causes the display unit 4 to display virtual images representing the progress of the series of obtaining operations of the capsule medical apparatus 62. By watching the virtual images displayed on the display unit 4, the user can easily know the process from when the capsule medical apparatus 62 in the subject 1 starts the series of obtaining operations until it completes them.

Figure 15:
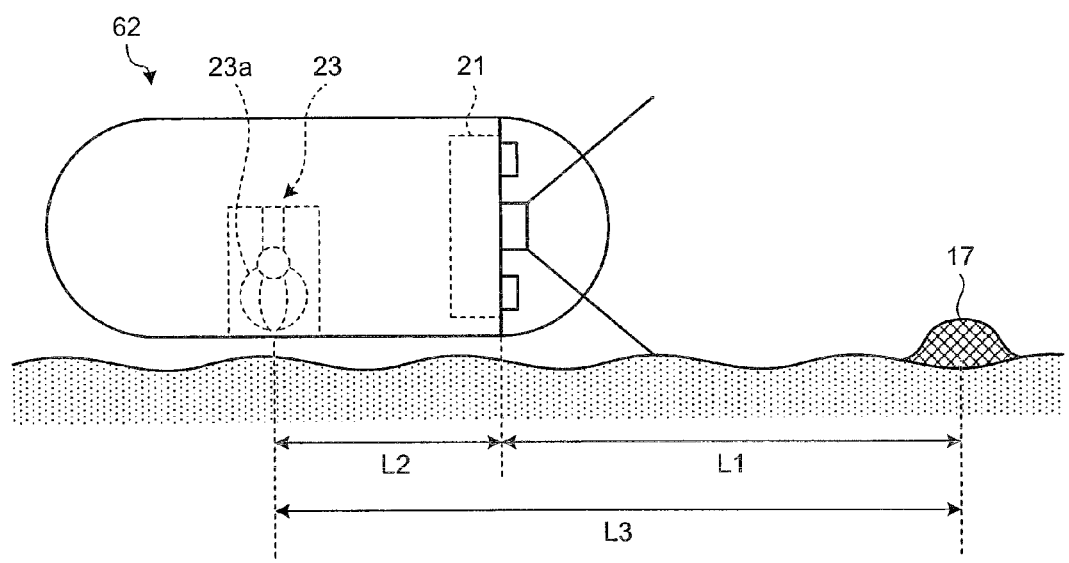
FIG. 15 is a schematic diagram for explaining a distance calculating process for calculating a distance between the capsule medical apparatus in a subject and a target site.

A distance calculating process for calculating a distance between the capsule medical apparatus 62 and a target site in the subject 1 that is performed by the distance calculator 70c is explained below. FIG. 15 is a schematic diagram for explaining the distance calculating process for calculating a distance between the capsule medical apparatus 62 and the target site in the subject 1. Hereinafter, the distance calculating process performed by the distance calculator 70c is explained, taking a lesion 17 in the body site shown in FIG. 15 as an example of the target site in the subject 1.

The distance calculator 70c receives pixel information about the in-vivo images captured by the capsule medical apparatus 62 in the subject 1 and position information about the position of the lesion 17 specified in the in-vivo images. The in-vivo images are captured by the capsule medical apparatus 62 in the state shown in FIG. 15, and represent the lesion 17 in the subject 1 when they are displayed on the display unit 4 outside the subject 1. The position information about the lesion 17 corresponds to the pixel position of the lesion 17 contained in the in-vivo images displayed on the display unit 4, and it is input by the input unit 8.

The distance calculator 70c calculates a distance L1 between the imaging unit 21 and the lesion 17 based on the pixel information about the in-vivo images and the position information about the lesion 17. The distance calculator 70c adds the distance L1 to a distance L2 between the imaging unit 21 and the obtaining unit 23a of the biopsy mechanism 23 in the capsule medical apparatus 62, thereby calculating a distance L3 between the lesion 17 and the obtaining unit 23a. The distance L2 is constant because the relative position between the imaging unit 21 and the obtaining unit 23a of the biopsy mechanism 23 in the capsule medical apparatus 62 is fixed. The distance L2 is previously set as an operation parameter of the distance calculator 70c.

The control unit 70 outside the subject 1 controls the magnetic direction of the magnetic-field generator 5 or the position of the moving unit 7 based on the distance L3 between the lesion 17 and the obtaining unit 23a, which is calculated by the distance calculator 70c. Accordingly, the position of the biopsy mechanism 23 (specifically, the obtaining unit 23a) of the capsule medical apparatus 62 and the position of the lesion 17 can be adjusted with high accuracy.

Figure 17A:
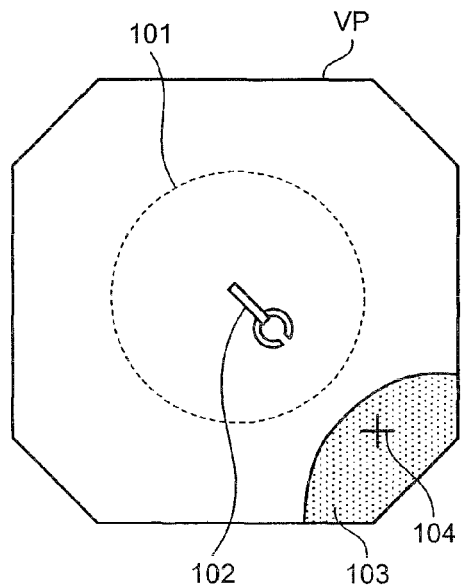
FIGS. 17A and 17B are schematic diagrams of virtual images obtained when a series of obtaining operations for obtaining a tissue are started.
Figure 17B:
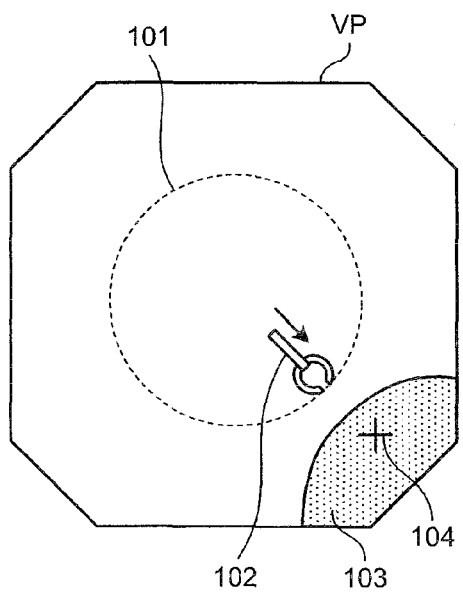
Figure 18A:
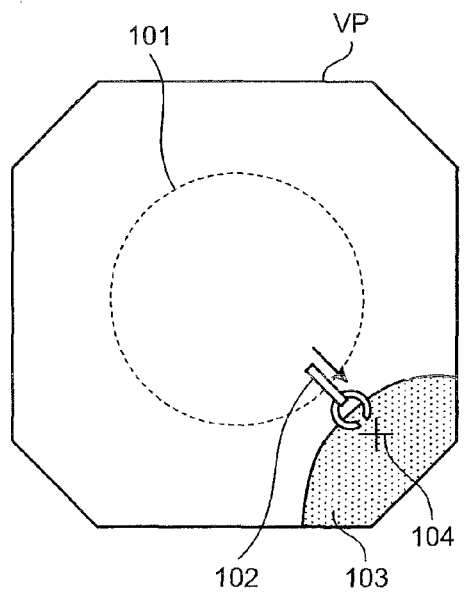
FIGS. 18A and 18B are schematic diagrams of virtual images obtained when the obtaining unit protrudes from a capsule casing during the series of obtaining operations.
Figure 18B:
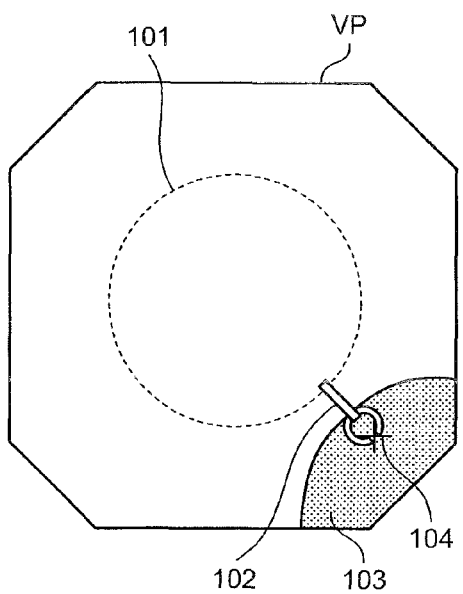
Figure 19A:
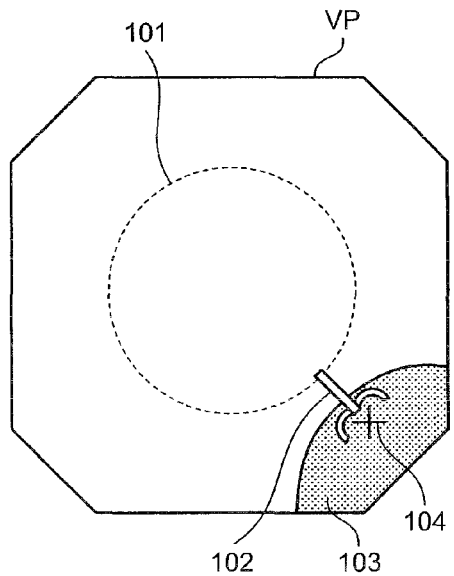
FIGS. 19A and 19B are schematic diagrams of virtual images obtained when the obtaining unit catches a tissue of a body site during the series of obtaining operations.
Figure 19B:
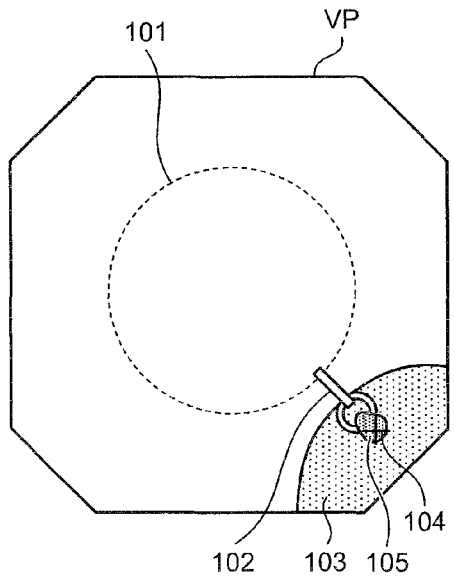
Figure 20A:
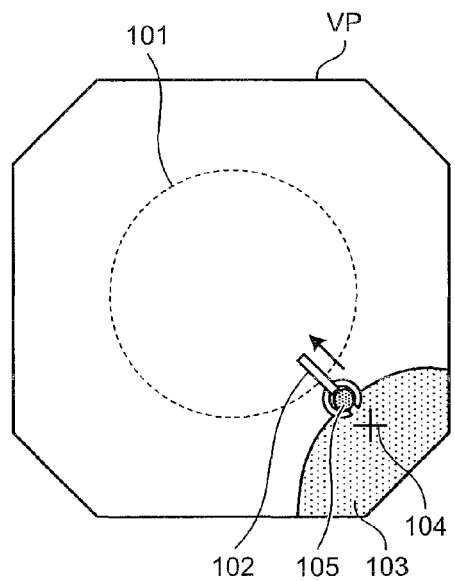
FIGS. 20A and 20B are schematic diagrams of virtual images obtained when the obtaining unit obtains a tissue in the series of obtaining operations.
Figure 20B:
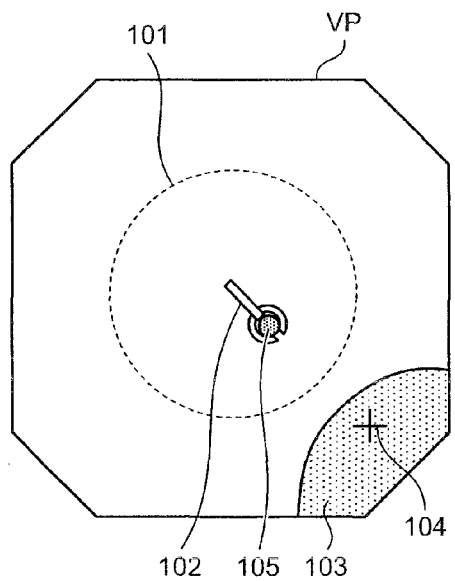

Operations of the control unit 70 outside the subject 1 for causing the display unit 4 to display virtual images representing the progress of the series of obtaining operations of the capsule medical apparatus 62 in the subject 1 are explained below. FIG. 16 is a schematic diagram of a specific example of a virtual image displayed on the display unit 4 outside the subject 1. FIGS. 17 to 20 are examples of virtual images that are sequentially displayed on the display unit 4 in accordance with the series of obtaining operations of the capsule medical apparatus 62. Specifically, FIGS. 17A and 17B are schematic diagrams of virtual images obtained when the series of obtaining operations for obtaining a tissue are started. FIGS. 18A and 18B are schematic diagrams of virtual images obtained when the obtaining unit 23a protrudes from the capsule casing 20 during the series of obtaining operations. FIGS. 19A and 19B are schematic diagrams of virtual images obtained when the obtaining unit 23a captures a tissue of a body site during the series of obtaining operations. FIGS. 20A and 20B are schematic diagrams of virtual images obtained when the obtaining unit 23a obtains a tissue in the series of obtaining operations. FIGS. 17 to 20 show only virtual images corresponding to the progress of the series of obtaining operations to easily explain the operations for displaying virtual images.

When the control unit 70 sets the operation mode to the virtual mode based on instruction information input by the input unit 8, the control unit 70 causes the display unit 4 to display a virtual image VP that represents a progress of the series of obtaining operations of the capsule medical apparatus 62 in the subject 1 as shown in FIG. 16. Specifically, the virtual-image processor 70d reads, from the storage unit 9, a virtual outline image 101 that represents the outline of the capsule medical apparatus 62, a virtual treatment-unit image 102 that represents the obtaining unit 23a of the biopsy mechanism 23, and a virtual tissue image 103 that represents a tissue to be obtained. The virtual-image processor 70d then generates a virtual image VP containing the virtual outline image 101, the virtual treatment-unit image 102, the virtual tissue image 103, and a target mark 104 that represents the position of the target site input by the input unit 8. The control unit 70 displays the virtual image VP in a predetermined display area on the display unit 4.

The virtual-image processor 70d may generate a virtual image VP by superposing the virtual outline image 101, the virtual treatment-unit image 102, and the virtual tissue image 103 on the real in-vivo image. Alternatively, a virtual image may be generated that represents the relative position between the virtual outline image 101, the virtual treatment-unit image 102, and the virtual tissue image 103, without using a real in-vivo image. Alternatively, the virtual image processor 70d may use, as the virtual tissue image 103, an image of a target site, such as a lesion, that is selected from a real in-vivo image by the input unit 8. Alternatively, the virtual image processor 70d may detect the outline and size of the target site contained in the real in-vivo image, and generate, ad the virtual tissue image 103, a virtual tissue image that corresponds to the detected outline and size. The control unit 70 may cause the display unit 4 to display the virtual image VP and a real in-vivo image SP together as shown in FIG. 16 when displaying the virtual image VP on the display unit 4 (i.e., in the virtual mode). Alternatively, the control unit 70 may cause the display unit 4 to display only the virtual image VP.

In the capsule medical apparatus 62 in the subject 1 that starts the series of obtaining operations for obtaining a desired tissue (for example, the lesion 17), the obtaining unit 23a of the biopsy mechanism 23 starts moving toward the lesion 17 in the subject 1 as described above. In this case, the virtual-image processor 70d first generates a virtual image VP that represents an initial state before the obtaining unit 23a starts moving. Thereafter, the virtual-image processor 70d sequentially generates virtual images representing that the obtaining unit 23a moves toward the lesion 17. The control unit 70 causes the display unit to display the virtual image VP representing the initial state (Phase C1) and then sequentially displays the virtual images VP in which the virtual treatment-unit image 102 shifts in accordance with the real movement of the obtaining unit 23a as shown in FIG. 17B (Phase C2). In Phase C2, the virtual treatment-unit image 102 in the virtual image VP displayed on the display unit 4 is displayed inside the virtual outline image 101 before the obtaining unit 23a actually protrudes from the capsule casing 20. The virtual treatment-unit image 102 sequentially shifts to the target mark 104 in the virtual tissue image 103 depending on the distance that the obtaining unit 23a actually moves.

Subsequently, the obtaining unit 23a of the biopsy mechanism 23 protrudes from the capsule casing 20 as it moves toward the lesion 17, and then contacts with the lesion 17. In this case, the virtual-image processor 70d generates a virtual image VP that represents that the obtaining unit 23a protrudes from the capsule casing 20. Thereafter, the virtual-image processor 70d generates a virtual image VP that represents that the obtaining unit 23a contacts with the lesion 17. When the virtual-image processor 70d receives, from the capsule medical apparatus 62, the operation state information corresponding to the detection result from the contact sensor 65, it generates a virtual image VP that represent that the obtaining unit 23a contacts with the lesion 17. Alternatively, when the distance that the obtaining unit 23a moves, which is represented by the operation state information received from the capsule medical apparatus 62, is equal to or larger than a predetermined value, the virtual-image processor 70d generates a virtual image VP representing that the obtaining unit 23a contacts with the lesion 17.

The control unit 70 causes the display unit 4 to display the virtual image VP representing that the obtaining unit 23a protrudes as shown in FIG. 18A (Phase C3) and then causes the display unit 4 to display the virtual image VP representing that the obtaining unit 23a contacts with the lesion 17 as shown in FIG. 18B (Phase C4). Even when the virtual treatment-unit image 102 does not reach the target mark 104 in the virtual image VP, the control unit 70 causes the display unit 4 to display the virtual image VP in Phase C4 after receiving the operation state information corresponding to the detection result from the contact sensor 65. Similarly, when the distance that the obtaining unit 23a moves, which is represented by the operation state information received from the capsule medical apparatus 62, is equal to or larger than the predetermined value, the control unit 70 causes the display unit 4 to display the virtual image VP in Phase C4.

In Phase C3, as the obtaining unit 23a protrudes actually, the virtual treatment-unit image 102 in the virtual image VP displayed on the display unit 4 gradually shifts toward the target mark 104 and protrudes from the virtual outline image 101. Thereafter, the virtual treatment-unit image 102 keeps shifting depending on the distance that the obtaining unit 23a moves. In Phase C4, the virtual treatment-unit image 102 in the virtual image VP displayed on the display unit 4 shifts depending on the distance that the obtaining unit 23a moves, and the virtual treatment-unit image 102 reaches the position of the target mark 104 representing the lesion 17. In this case, the virtual tissue image 103 is displayed on the display unit 4 such that it is represented that the obtaining unit 23a contacts with the lesion 17.

It suffices that the virtual tissue image 103 is displayed differently before and after it is represented that that the obtaining unit 23a contacts with the lesion 17. The virtual tissue image 103 may be displayed in different colors, different luminance, different lighting patterns, or combination of them before and after it is represented that that the obtaining unit 23a contacts with the lesion 17. Alternatively, instead of changing the display of the virtual tissue image 103, the background color of the virtual image VP may be changed, or the display (color, luminance, or lighting pattern) of the virtual treatment-unit image 102 may be changed. Alternatively, message information representing that the obtaining unit 23a contacts with the lesion 17 may be displayed on the display unit 4.

When the obtaining unit 23a contacts with the obtaining unit 23a of the biopsy mechanism 23, the obtaining unit 23a of the biopsy mechanism 23 opens or closes its forceps-shaped tips, and captures (holds) the lesion 17. In this case, the virtual-image processor 70d generates a virtual image VP that represents that the obtaining unit 23a opens its forceps-shaped tips, and then generates a virtual image VP that represents that the obtaining unit 23a closes its forceps-shaped tips and captures the lesion 17. As shown in FIG. 19A, the control unit 70 causes the display unit 4 to display the virtual image VP representing that the obtaining unit 23a opens its forces-shaped tips (Phase C5) and then causes the display unit 4 to display the virtual image VP representing that the obtaining unit 23a captures the lesion 17 (Phase C6).

In Phase C5, the virtual treatment-unit image 102 in the virtual image VP displayed on the display unit 4 stops shifting when the obtaining unit 23a stops moving actually, and the tips of the virtual treatment-unit image 102 open as the obtaining unit 23a opens its forceps-shaped tips. In Phase C6, the tips of the virtual treatment-unit image 102 in the virtual image VP displayed on the display unit 4 closes as the obtaining unit 23a closes its forceps-shaped tips actually, and the virtual treatment-unit image 102 captures a virtual tissue image 105 that represents the lesion 17. The virtual tissue image 103 then returns from the state where it represents that the obtaining unit 23a contact with the lesion 17 to the original display state.

After the obtaining unit 23a captures the lesion 17, it excises the lesion 17 from the body site of the subject 1, and the obtaining unit 23a that holds the lesion 17 is then housed in the capsule casing 20. In this case, the virtual-image processor 70d generates a virtual image VP that represents that the obtaining unit 23a excises the lesion 17, and then generates a virtual image VP that represents that the obtaining unit 23a that holds the lesion 17 is housed in the capsule casing 20. The control unit 70 causes the display unit 4 to display the virtual image VP representing that the obtaining unit 23a excises the lesion 17 as shown in FIG. 20A (Phase C7). Thereafter, the control unit 70 causes the display unit 4 to display the virtual image VP representing that the obtaining unit 23a that holds the lesion 17 is housed in the capsule casing 20 as shown in FIG. 20B (Phase C8).

In Phase C7, the virtual treatment-unit image 102 in the virtual image VP displayed on the display unit 4 captures the virtual tissue image 105 representing the lesion 17, as in accordance with the operation of the obtaining unit 23a for excising a tissue. Thereafter, the virtual treatment-unit image 102 shifts toward the virtual outline image 101 depending on the distance that the obtaining unit 23a moves. In Phase C8, the virtual treatment-unit image 102 that holds the virtual tissue image 105 representing the lesion 17 shifts toward the virtual outline image 101, and then shifts to the inner side of the virtual outline image 101. The virtual treatment-unit image 102 stops shifting when the obtaining unit 23a stops moving actually.

While the capsule medical apparatus 62 in the subject 1 performs the series of obtaining operations, the series of virtual images VP displayed on the display unit 4, which are sequentially displayed as described above, allow the user to know easily the progress of the series of obtaining operations. By watching the information (the successful/unsuccessful information representing whether a tissue is successfully obtained and the series of virtual images VP) on the display unit 4, the user can easily know not only whether a tissue is successful obtained but also the progress of the series of obtaining operations of the capsule medical apparatus 62 for obtaining a tissue. This reduces the user's anxious when the user operates the capsule medical apparatus 62 in the subject 1 which is difficult to watch directly, and allows the user to easily operate the capsule medical apparatus in the subject 1, using the virtual images.

As explained above, in the third embodiment of the present invention, the detecting units of the capsule medical apparatus detect the progress of the series of obtaining operations for obtaining a tissue from a body site of the subject. The operation state information that represents the detected progress of the series of obtaining operations is then transmitted to the outside sequentially. The control unit outside the subject generates virtual images that represent the progress of the series of obtaining operations based on the operation state information received from the capsule medical apparatus. The control unit causes the display unit to display the virtual images sequentially. Other elements of the third embodiment are identical to those of the first embodiment. With this configuration, using with the virtual images, the user can easily confirm not only whether a tissue is successfully obtained but also the progress of the operations (for example, the progress of the series of obtaining operations) of the capsule medical apparatus in the subject that is difficult to watch directly. This leads to a capsules medical apparatus and a medical system with the same functions and results as those of the first embodiment, reduces user's anxious during the series of obtaining operations that is difficult to watch directly, and improves efficiency of the series of obtaining operations.

In the first to third embodiments and Modifications 1 and 2, when the capsule medical apparatus succeeds in obtaining a tissue, the capsule medical apparatus transmits the successful/unsuccessful information representing that a tissue is successfully obtained, and the external display unit displays the successful/unsuccessful information representing the success. Alternatively, when the capsule medical apparatus does not succeed (fails) in obtaining a tissue, the capsule medical apparatus may transmit successful/unsuccessful information representing that a tissue is not obtained to the outside, and the external display unit may display the successful/unsuccessful information representing the failure. In this case, the capsule medical apparatus may repeat the series of obtaining operations in response to the failure in obtaining a tissue. Alternatively, after completing one cycle of the series of obtaining operations, the capsule medical apparatus may wait a control signal from the outside. In this case, the capsule medical apparatus repeats the series of obtaining operations based on a received control signal from the external device.

In the first to third embodiments and Modifications 1 and 2, successful/unsuccessful information representing whether a tissue is successfully obtained is transmitted to the outside. Alternatively, when a tissue is successfully obtained, sound information representing the success may be output to the outside. Alternatively, when a tissue is not obtained, successful/unsuccessful information representing the failure may be output to the outside. In this case, the capsule medical apparatus incorporates a sound output unit configured to output sound information such as various types of pattern sounds or voice. The sound output unit outputs sound information representing success or failure depending on whether a tissue is successfully obtained under the control by the control unit of the capsule medical apparatus.

In the third embodiment, the series of virtual images displayed on the display unit are used to allow a user to know the progress of the series of obtaining operations of the capsule medical apparatus in the subject. Alternatively, lamp lighting indication may be used to represent a relative poison between a tissue to be obtained, such as a lesion, and a tool (for example, the obtaining unit 23a that obtains a tissue) in the capsule medical apparatus. Alternatively, a message or pattern sounds that represents the progress of the series of obtaining operations may be output.

In the third embodiment, the progress of the series of obtaining operations is represented using the virtual images of the forceps-shaped obtaining unit that protrudes from or retracts into the capsule casing. Alternatively, as in the case of the second embodiment and Modifications 1 and 2, virtual images that represent the relative position between a tissue and the tissue obtaining unit (the biopsy mechanism 33) that excises a tissue, which is sucked into the housing unit, to obtain the tissue may be generated. In this case, the virtual images may represent the progress of the series of obtaining operation.

Figure 21A:
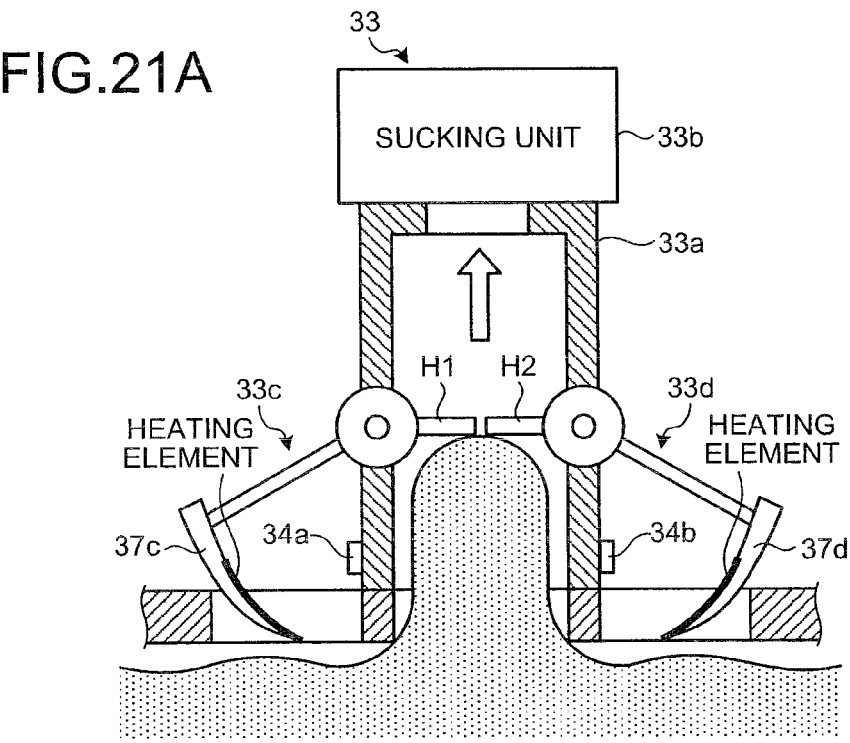
FIGS. 21A and 21B are schematic diagrams that show an example of phases where a biopsy mechanism of the capsule medical apparatus according to the second embodiment obtains a tissue from the body site while arresting hemorrhage.
Figure 21B:
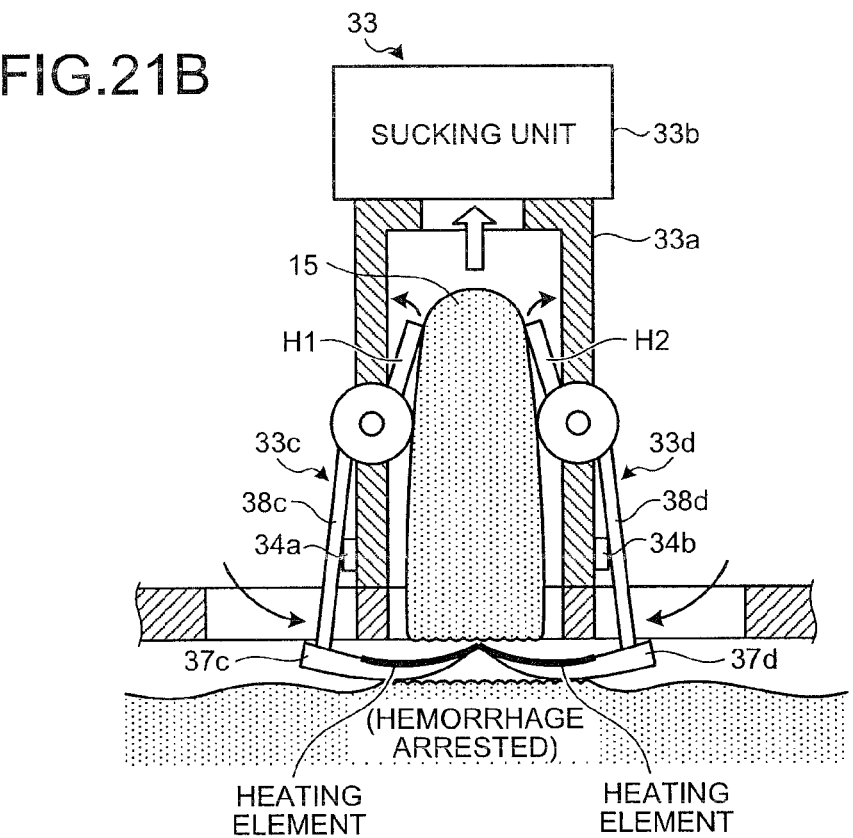

In the first to third embodiments and Modifications 1 and 2, the obtaining unit 23a or the excising units 33c and 33d excise a tissue. Furthermore, a hemorrhage arresting process for arresting hemorrhage of the excised tissue may be performed. Specifically, the capsule medical apparatus according to the second embodiment or Modification 1 or 2, for example, heating elements may be provided to the blades 37c and 37d of the excising units 33c and 33d as shown in FIGS. 21A and 21B. In this case, a tissue is excised while hemorrhage is arrested due to action of the heating element at the excised surface of the tissue. The heating elements of the blades 37c and 37d function as a hemorrhage arresting unit. The heating elements generate heat by power supplied from the power unit 27, and blood is clotted at the excised surface of the tissue by the heat, so that hemorrhage is arrested. The power source of the heating elements may be a power receiving coil (not shown) that wirelessly supplies power from outside the subject to the heating elements.

Figure 22:
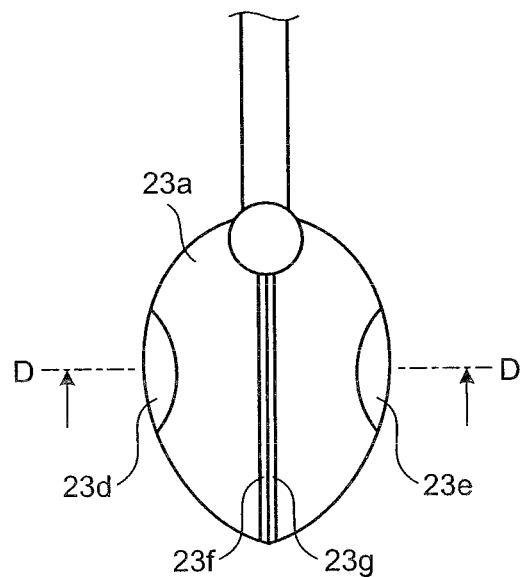
FIG. 22 is a schematic diagram of a modification of the obtaining unit of the biopsy mechanism.
Figure 23:
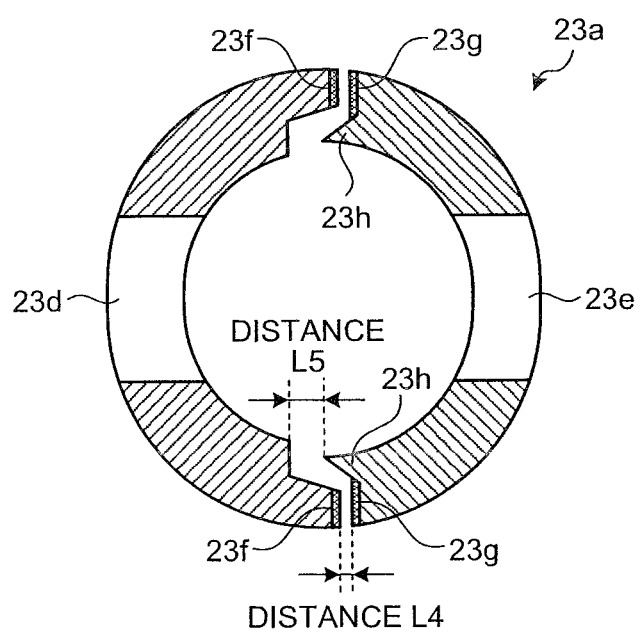
FIG. 23 is a schematic cross-sectional view of the obtaining unit shown in FIG. 22, taken along line D-D shown in FIG. 22.
Figure 24:
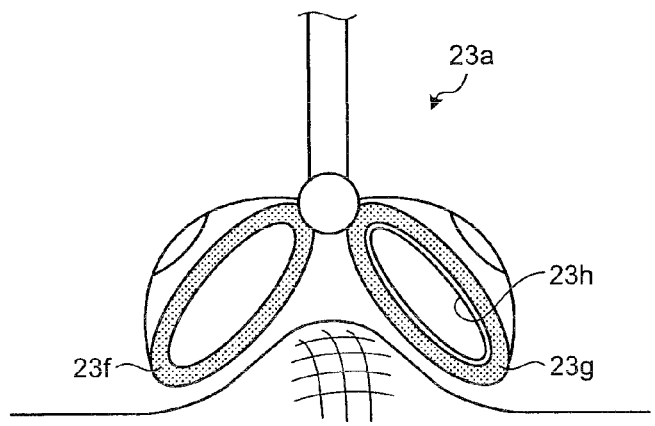
FIG. 24 is a schematic diagram that shows an example of the state where the obtaining unit obtains a tissue by excision while arresting hemorrhage.

In the capsule medical apparatuses according to the first and third embodiments, for example, a sandwiching hemorrhage arresting members 23f and 23g and a blade 23h may be provided to the function side (the inner side) of the obtaining unit 23a as shown in FIGS. 22 and 23. In this case, the blade 23h excises a tissue while the hemorrhage arresting members 23f and 23g sandwich the tissue in between and arrest hemorrhage. Specifically, the hemorrhage arresting members 23f and 23g are arranged on the periphery of the forceps-shaped tips of the obtaining unit 23a. When the obtaining unit 23a is closed, the distance between the hemorrhage arresting members 23f and 23g is a distance L4. The blade 23h is formed in a circle on the inner side of the hemorrhage arresting member 23g. When the obtaining unit 23a is closed, the distance between the blade 23h and the surface of the body cavity is L5 which is slightly lager than the distance L4. As shown in FIG. 24, the obtaining unit 23a having the above configuration sandwiches a tissue between the hemorrhage arresting members 23f and 23g. While pressurizing the tissue, the obtaining unit 23a excises the tissue using the blade 23h. Thereafter, the obtaining unit 23a sandwiches the tissue between the hemorrhage arresting members 23f and 23g and continues pressurizing the tissue for a predetermined time, thereby arresting hemorrhage of the tissue.

The above-described hemorrhage arresting member (the heating elements of the blades 37c and 37d or the hemorrhage arresting members 23f and 23g of the obtaining unit 23a) may be configured to not only arrest hemorrhage by the thermal process (clotting) or the pressurizing process on a tissue but also apply a haemostatic such as alcohol on the excised surface of the tissue.

In the first to third embodiments and Modifications 1 and 2, the capsule medical apparatuses each include a single biopsy mechanism. Alternatively, each of the capsule medical apparatuses may include a plurality of biopsy mechanisms. This leads to a capsule medical apparatus that can obtain a tissue inside a subject for a plurality of times.

Figure 25:
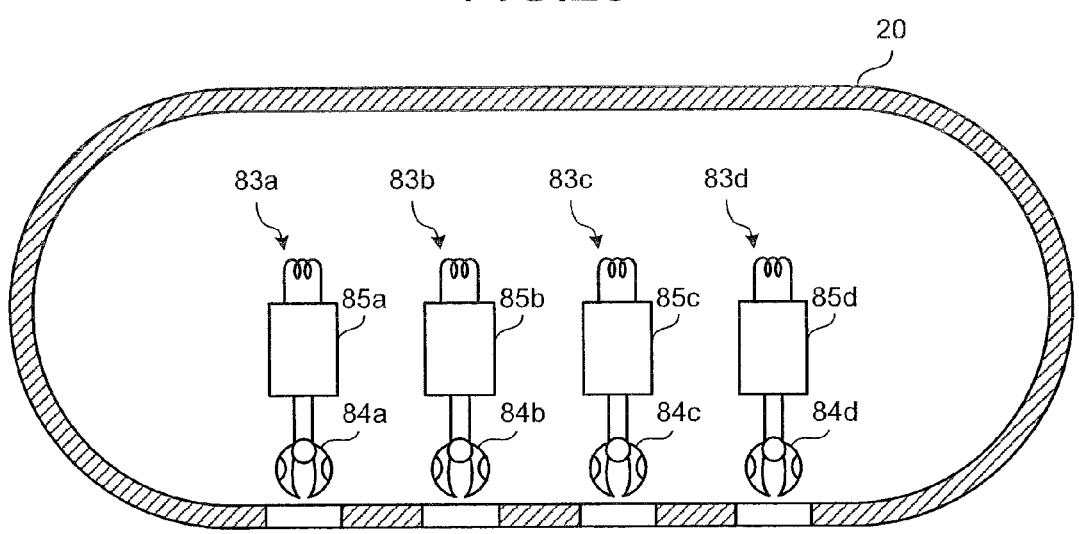
FIG. 25 is a schematic diagram of an example of a capsule medical apparatus that includes a plurality of biopsy mechanisms.

The biopsy mechanisms 23 and 33 according to the first to third embodiments or Modifications 1 and 2 may be used as the biopsy mechanisms that are incorporated in the capsule medical apparatus. Alternatively, the biopsy mechanisms 23 and 33 may be biopsy mechanisms that are driven by an eternal magnetic field that is eternally applied thereto. For example, as shown in FIG. 25, the biopsy mechanisms 83a to 83d arranged in the capsule casing 20 are driven by external magnetic fields, and include obtaining units 84a to 84d and drive units 85a to 85d, respectively. The obtaining units 84a to 84d have the same configuration as that of the obtaining unit 23a, and operate due to the action of the drive units 85a to 85d as the obtaining unit 23a does. Piezoelectric devices (such as PZT) of different resonance frequencies and power receiving coils are used for the drive units 85a to 85d. Each of the drive units 85a to 85d is driven when the corresponding coil is applied with an external magnetic field, a drive current is generated, and the piezoelectric device resonates. By controlling the frequencies of external magnetic fields applied to the drive units 85a to 85d, the obtaining units 84a to 84d can be operated arbitrarily (a tissue can be obtained).

Figure 26:
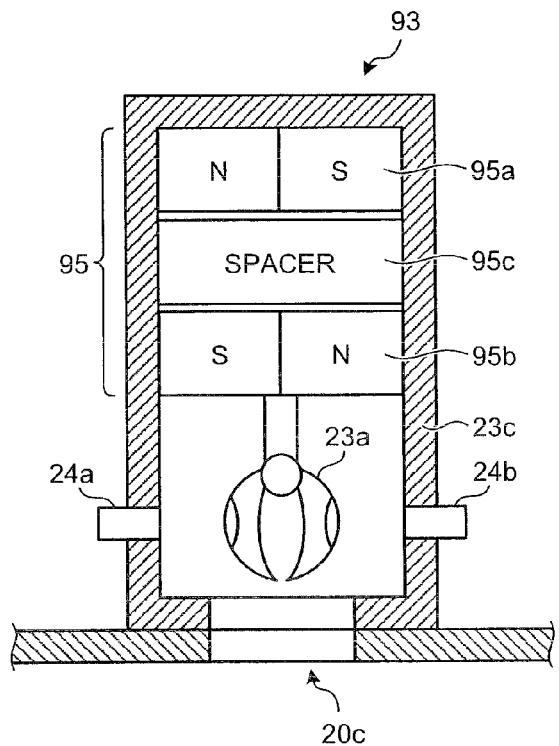
FIG. 26 is a schematic diagram of an example of a biopsy mechanism that is driven by an external magnetic field.

A drive unit of the biopsy mechanism that is driven by an external magnetic field may include two magnets. For example, as shown in FIG. 26, the biopsy mechanism 93 includes the obtaining unit 23a and a drive unit 95 that is driven by an external magnetic field. The drive unit 95 includes a pair of magnets 95a and 95b and a spacer 95c positioned between the magnets 95a and 95b. The magnet 95a is arranged in the housing unit 23c on one end (the end opposite to the opening 20c) of the housing unit 23c. The magnet 95b is arranged in a position closer to the opening 20c than that of the magnet 95a, and the spacer 95c is arranged between the magnets 95a and 95b. The magnets 95a and 95b are positioned in the housing unit 23c in the state where the obtaining unit 23a is housed in the housing unit 23c such that the north pole of the magnet 95a and the south pole of the magnet 95b are opposed to each other and the south pole of the magnet 95a and the north pole of the magnet 95b are opposed to each other. The magnets 95a and 95b are attracted with each other by magnetic attraction via the spacer 95c. In contrast, when the same poles of the magnets 95a and 95b are opposed to each other due to external magnetic fields applied to the drive unit 95 from outside the subject, the magnets 95a and 95b generate magnetic repulsion via the spacer 95c. As a result, the magnet 95b moves toward the opening 20c. The obtaining unit 23a then moves with the magnet 95b, protrudes from the opening 20c, and obtains a tissue as in the case of the first and third embodiments. Thereafter, the different poles of the magnets 95a and 95b are opposed to each other due to an external magnetic field applied to the drive unit 95 from outside the subject. In this case, the magnet 95b moves toward the magnet 95a due to magnetic attraction, and the magnets 95a and 95b attract with each other via the spacer 95c. The obtaining unit 23a moves with the magnet 95b and is housed in the housing unit 23c.

Figure 27:
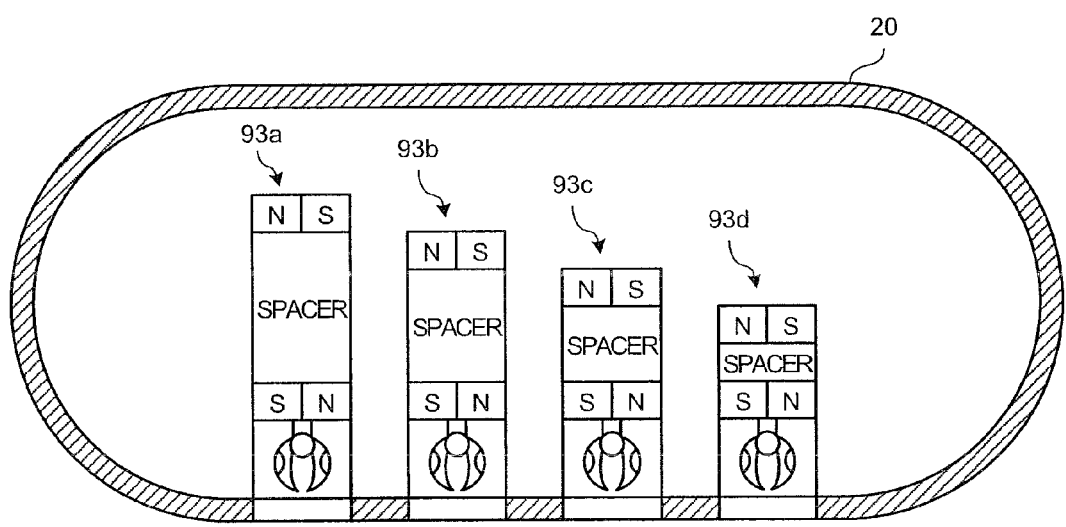
FIG. 27 is a schematic diagram of another example of the capsule medical apparatus including a plurality of biopsy mechanism.

The biopsy mechanisms 93 including the magnets 95a and 95b may be provided in the capsule medical apparatus. For example, as shown in FIG. 27, the capsule medical apparatus may includes a plurality of biopsy mechanisms 93a to 93d arranged in the capsule casing 20. The biopsy mechanisms 93a to 93d each have the same configuration as that of the biopsy mechanism 93 except that spacers of the biopsy mechanisms 93a to 93d have different thicknesses, respectively. In each of the biopsy mechanisms 93a to 93d, two magnets between which a spacer is arranged have different magnetic attraction. Therefore, by changing the magnetic strengths of external magnetic fields that are applied to the biopsy mechanisms 93a to 93d from smaller one to larger one, the order of operations of the biopsy mechanisms 93a to 93d can be controlled.

Figure 28:
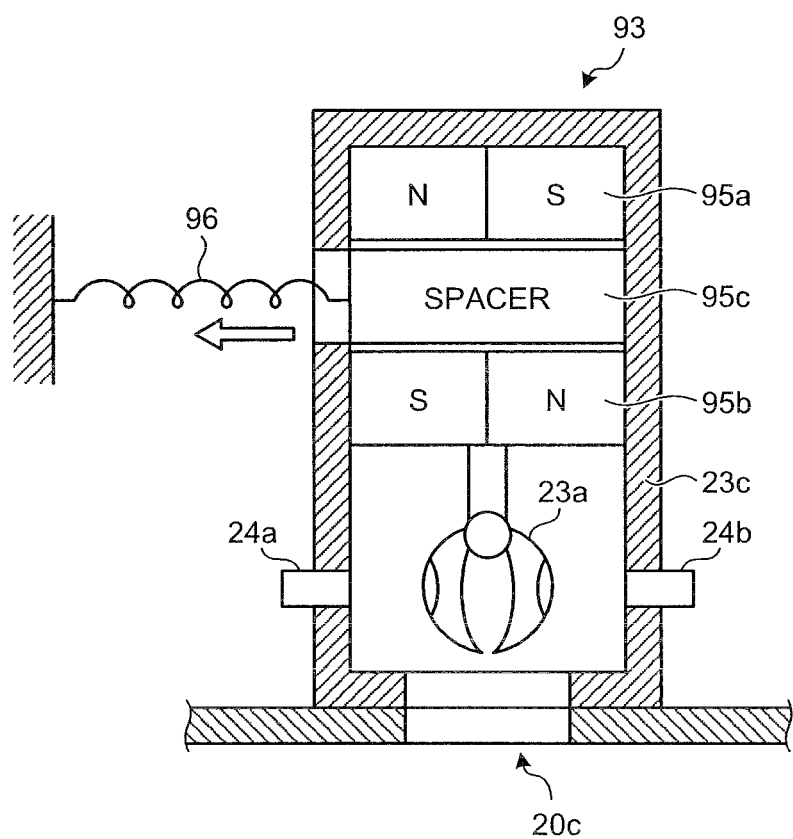
FIG. 28 is a schematic diagram of a modification of the biopsy mechanism that is driven by an external magnetic field.

The biopsy mechanism 93 may be configured such that the spacer 95c between the magnets 95a and 95b is removable from the biopsy mechanism 93. For example, as shown in FIG. 28, the spacer 95c of the biopsy mechanism 93 is connected to an external unit outside the housing unit 23c via a spring 96. The spring 96 is tensed when the spacer 95c is housed in the housing unit 23c (i.e., when the spacer 95c is present between the magnets 95a and 95b), and it maintains a force (compression force) to pull the spacer 95c to outside the housing unit 23c. The spacer 95c is fixed between the magnets 95a and 95b by magnetic attraction between the magnets 95a and 95b. When the magnet 95b moves toward the opening 20c (moves away from the magnet 95a) by application of an external magnetic field, the magnetic attraction between the magnets 95a and 95b weakens, so that the spacer 95c is excluded from the space between the magnets 95a and 95b due to a compression force of the spring 96. Thereafter, different poles of the magnets 95a and 95b are opposed to each other due to a magnetic field applied from outside of the subject. In this case, the magnet 95b moves toward the magnet 95a by magnetic attraction. The spacer 95c is excluded from the housing unit 23c to the outside by the action of the spring 96 as described above. Therefore, the magnets 95a and 95b directly contact with each other closely by magnetic attraction stronger than that obtained when the spacer is present between the magnets 95a and 95b. The magnets 95a and 95b closely contacting with each other do not separate by an external magnetic field and keeps closely contacting with each other. The obtaining unit 23a fixed to the magnet 95b never operates (for example, protrudes to outside the capsule casing) again once it obtains a tissue, which prevents contamination between tissues.

In the capsule medical apparatuses and medical systems according to the above embodiments, the tissue obtaining unit performs the series of obtaining operations for obtaining a tissue from a body site of a subject; the detecting unit detects the state of the tissue obtaining unit that varies depending on whether a tissue is successfully obtained by performing the series of obtaining operations; the output unit outputs information representing whether a tissue is successfully obtained to outside the subject; and the control unit determines whether a tissue is successfully obtained based on the state of the tissue obtaining unit, which is detected by the detecting unit, and causes the output unit to output the information representing the determination on whether a tissue is successfully obtained. With this configuration, an external user can know that a tissue is successfully obtained before the obtained tissue is taken out of the subject (collected). This leads to a capsule medical apparatus and a medical system that allow a user to confirm whether a tissue is successfully obtained from a body site of a subject, while the capsule medical apparatus is still positioned in a desired body site in the subject.

In addition, in the capsule medical apparatuses and medical systems according to the above embodiments, the detecting units of the capsule medical apparatus detect the progress of the series of obtaining operations for obtaining a tissue from a body site of a subject, and sequentially transmits the operation state information representing the detected progress of the series of obtaining operations to outside the subject; and the control unit outside the subject generates virtual images representing the progress of the series of obtaining operations based on the operation state information received from the capsule medical apparatus, and causes the display unit to display the generated virtual images. With this configuration, using the virtual images, not only whether a tissue is successfully obtained but also the progress of the series of obtaining operations in the subject, which is difficult to watch directly, can be easily represented. This reduces the user's anxious when performing the series of obtaining operations, which is difficult to watch directly, which improves efficiency in the series of obtaining operations.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule medical apparatus comprising:
   a capsule casing:
   a tissue obtaining unit having: a forceps-shaped obtaining unit configured to protrude from and retract into the capsule casing to obtain a tissue from a body site of a subject; and a housing unit configured to house the forceps-shaped obtaining unit;

a detecting unit that detects a state of the tissue obtaining unit that varies depending on whether the tissue obtaining unit succeeds in obtaining the tissue, the detecting unit being a photosensor having a light emitter and a light receiver, the light emitter and the light receiver being arranged on a wall of the housing unit such that the light emitter and the light receiver face each other;

an output unit that outputs information representing whether the tissue obtaining unit succeeds in obtaining the tissue to outside of the subject; and a control unit that determines whether the tissue obtaining unit succeeds in obtaining the tissue based on the state of the tissue obtaining unit, which is detected by the detecting unit, and causes the output unit to output the information representing whether the tissue obtaining unit succeeds in obtaining the tissue, the control unit being arranged in the capsule casing, wherein if the tissue obtaining unit does not succeed in obtaining the tissue, the control unit causes the tissue obtaining unit to perform a tissue obtaining operation again and causes the output unit to output the information representing the success in obtaining the tissue when the tissue obtaining unit succeeds in obtaining the tissue, and when the forceps-shaped obtaining unit is housed in the housing unit, the control unit determines whether the tissue is obtained in tips of the forceps-shaped obtaining unit based on whether the light receiver receives light from the light emitter.

2. The capsule medical apparatus according to claim 1, wherein the output unit is a transmitting unit that transmits the information that represents whether the tissue obtaining unit succeeds in obtaining the tissue to a receiving unit arranged outside the subject.

* * * * *